(12) United States Patent  
Williams et al.

(10) Patent No.: US 8,592,148 B2  
(45) Date of Patent: *Nov. 26, 2013

(54) FIELD-SWITCH SEQUENCING

(75) Inventors: John G. K. Williams, Lincoln, NE (US); Jon P. Anderson, Lincoln, NE (US)

(73) Assignee: Pacific Biosciences of California, Menlo Park, CA (US)

( * ) Notice: Subject to any disclaimer, the term of this patent is extended or adjusted under 35 U.S.C. 154(b) by 307 days.

This patent is subject to a terminal disclaimer.

(21) Appl. No.: 12/263,397

(22) Filed: Oct. 31, 2008

(65) Prior Publication Data

US 2011/0177496 A1    Jul. 21, 2011

Related U.S. Application Data

(63) Continuation of application No. 11/118,031, filed on Apr. 29, 2005, now Pat. No. 7,462,452.

(60) Provisional application No. 60/567,202, filed on Apr. 30, 2004.

(51) Int. Cl.
  *C12Q 1/68* (2006.01)
  *C07H 19/00* (2006.01)

(52) U.S. Cl.
  USPC .................................. 435/6.1; 536/22.1

(58) Field of Classification Search
  None
  See application file for complete search history.

(56) References Cited

U.S. PATENT DOCUMENTS

| | | | |
|---|---|---|---|
| 6,127,127 A | 10/2000 | Eckhardt et al. | |
| 6,232,075 B1 | 5/2001 | Williams | |
| 6,255,083 B1 | 7/2001 | Williams | |
| 6,306,607 B2 | 10/2001 | Williams | |
| 6,316,229 B1 | 11/2001 | Lizardi et al. | |
| 6,361,944 B1 | 3/2002 | Mirkin et al. | |
| 6,548,264 B1 | 4/2003 | Tan et al. | |
| 6,610,499 B1 | 8/2003 | Fulwyler et al. | |
| 6,762,048 B2 | 7/2004 | Williams | |
| 6,869,764 B2 | 3/2005 | Williams et al. | |
| 7,462,452 B2 | 12/2008 | Williams et al. | |
| 2002/0039738 A1 | 4/2002 | Williams et al. | |
| 2002/0042071 A1 | 4/2002 | Williams et al. | |
| 2002/0137047 A1 | 9/2002 | Baskin et al. | |
| 2002/0168678 A1 | 11/2002 | Williams et al. | |
| 2003/0044781 A1* | 3/2003 | Korlach et al. | 435/6 |
| 2003/0134807 A1 | 7/2003 | Hardin et al. | |
| 2003/0143581 A1 | 7/2003 | Franzen et al. | |
| 2003/0143598 A1 | 7/2003 | Garimella et al. | |
| 2003/0165859 A1 | 9/2003 | Nazarenko et al. | |
| 2003/0215816 A1* | 11/2003 | Sundararajan et al. | 435/6 |
| 2004/0023248 A1 | 2/2004 | O'Malley | |
| 2004/0067503 A1 | 4/2004 | Tan et al. | |
| 2004/0086914 A1* | 5/2004 | Cole et al. | 435/6 |
| 2005/0042633 A1 | 2/2005 | Williams | |

FOREIGN PATENT DOCUMENTS

| | | |
|---|---|---|
| WO | WO 99/49831 A2 | 10/1999 |
| WO | WO 2004/020654 A2 | 3/2004 |

OTHER PUBLICATIONS

Zhao et al. Journal of the American Chemical Society (2003) 125: 11474-11475.*
Rybak et al. Journal of Cell Physiology (1998) 176: 216-222.*
Martinez-Zaguilan et al. Biochemical Pharmacology (1999) 57: 1037-1046.*
Gerion et al. Journal of the American Chemical Society (2002) 124: 7070-7074.*
Anazawa, T. et al., "Electrophoretic Quantitation of Nucleic Acids without Amplification by Single-Molecule Imaging," *Analytical Chemistry*, Oct. 1, 2002, vol. 74, No. 19, pp. 5033-5038.
Braslavsky, I. et al., "Sequence information can be obtained from single DNA molecules," *PNAS*, Apr. 1, 2003, vol. 100, No. 7, pp. 3960-3964.
Femino, A.M. et al., "Visualization of Single RNA Transcripts in Situ," *Science*, Apr. 24, 1998, vol. 280, pp. 585-590.
Taylor, J.R. et al., "Probing Specific Sequences on Single DNA Molecules with Bioconjugated Fluorescent Nanoparticles," *Analytical Chemistry*, May 1, 2000, vol. 72, No. 9, pp. 1979-1986.
Curulli et al., "Bienzyme amperometric probes for choline and choline esters assembled with nonconducting electrosynthesized polymers," *Electroanalysis*, 2001, vol. 13, No. 3, pp. 236-242.
Heller et al., "Active microelectronic chip devices which utilize controlled electrophoretic fields for multiplex DNA hybridization and other genomic applications," *Electrophoresis*, 2000, vol. 21, pp. 157-164.
Kerman et al., "Electrochemical Coding of Single-Nucleotide Polymorphisms by Monobase-Modified Gold Nanoparticles," *Analytical Chemistry*, 2004, vol. 76, pp. 1877-1884.
Niemeyer, C.M., "Self-assembled nanostructures based on DNA: towards the development of nanobiotechnology," *Current Opinion in Chemical Biology*, 2000, vol. 4, pp. 609-618.
Ronaghi et al., "A sequencing method based on real-time pyrophosphate," *Science*, 1998, vol. 281, No. 5375, pp. 363 & 365.
Shih et al., "A 1.7-kilobase single-stranded DNA that folds into a nanoscale octahedron," *Nature*, 2004, vol. 427, No. 6975, pp. 618-621.
Sosnowski et al., "Rapid determination of single base mismatch mutations in DNA hybrids by direct electric field control," *Proceedings of the National Academy of Science USA*, 1997, vol. 94, pp. 1119-1123.
Yang et al., "Nanometer fluorescent hybrid silica paricle as ultrasensitive and photostable biological labels," Analyst, 2003, vol. 128, pp. 462-466.

* cited by examiner

*Primary Examiner* — Angela M Bertagna
(74) *Attorney, Agent, or Firm* — Kilpatrick Townsend & Stockton LLP

(57) ABSTRACT

The present invention provides novel compositions, methods and apparatus for DNA sequencing that can be performed, e.g., in a two-electrode chamber. The present invention also provides a method for sequencing a nucleic acid comprising immobilizing a plurality of complexes comprising a target nucleic acid, a primer nucleic acid, and a polymerase onto a surface, contacting the surface with a plurality of charged particles comprising a nucleotide phosphate by applying an electric field, reversing the electric field to transport unbound charged particles away from the surface, and detecting the incorporation of a nucleotide phosphate into a single molecule of the primer nucleic acid.

21 Claims, 15 Drawing Sheets

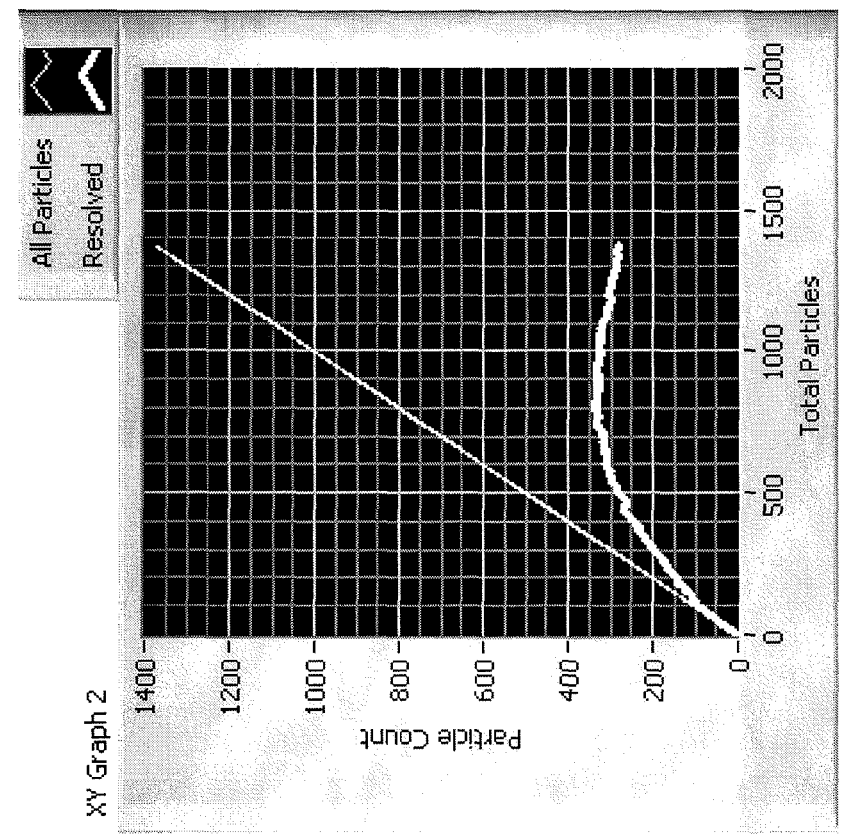
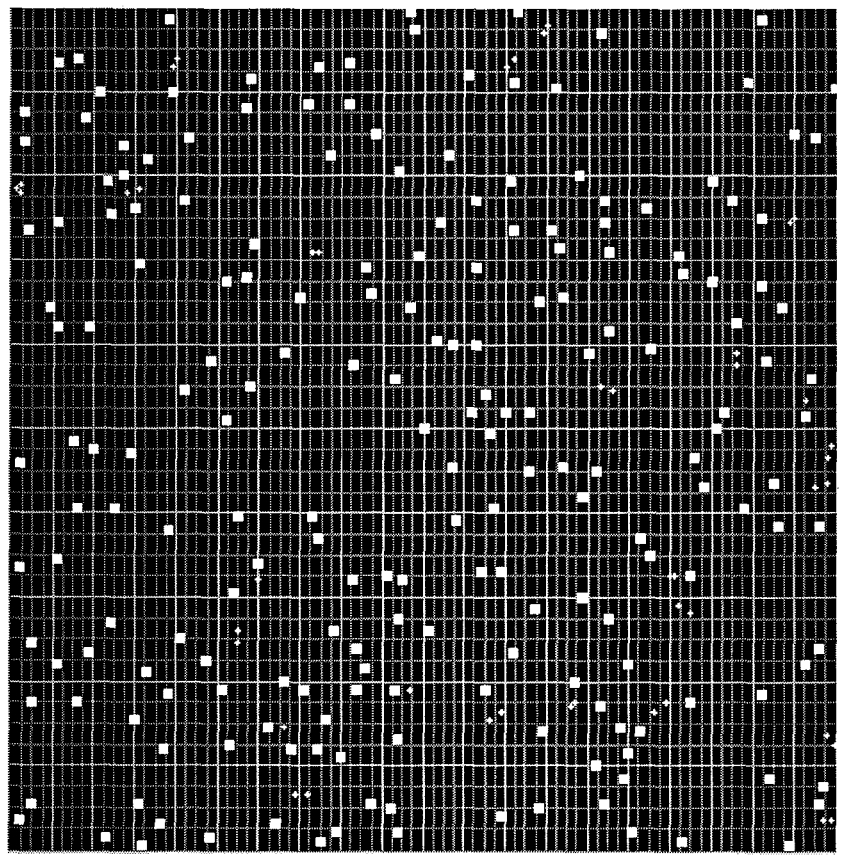
FIG. 6

Deprotection of BOC-PEG8-amine from PolyPure

Gamma phosphate labeled PEG reaction with dATP

SIA reaction with dCTP-PEG8-amine

Iodoacetimide activated dCTP-PEG coupling to SYBR-cysteine

FIELD-SWITCH SEQUENCING

CROSS-REFERENCE TO RELATED APPLICATIONS

This application is a continuation of U.S. patent application Ser. No. 11/118,031, filed on Apr. 29, 2005, issued as U.S. Pat. No. 7,462,452, which application claims the benefit of priority of U.S. Provisional Application No. 60/567,202, filed Apr. 30, 2004, both of which applications are incorporated herein by reference.

STATEMENT AS TO RIGHTS TO INVENTIONS MADE UNDER FEDERALLY SPONSORED RESEARCH OR DEVELOPMENT

The invention was made with government support under grant number 1 P01 HG003015 awarded by the National Institutes of Health. The government has certain rights in the invention.

BACKGROUND OF THE INVENTION

The primary sequences of nucleic acids are crucial for understanding the function and control of genes and for applying many of the basic techniques of molecular biology. In fact, rapid DNA sequencing has taken on a more central role after the goal to elucidate the entire human genome has been achieved. DNA sequencing is an important tool in genomic analysis as well as other applications, such as genetic identification, forensic analysis, genetic counseling, medical diagnostics, and the like. With respect to the area of medical diagnostic sequencing, disorders, susceptibilities to disorders, and prognoses of disease conditions can be correlated with the presence of particular DNA sequences, or the degree of variation (or mutation) in DNA sequences, at one or more genetic loci. Examples of such phenomena include human leukocyte antigen (HLA) typing, cystic fibrosis, tumor progression and heterogeneity, p53 proto-oncogene mutations, and ras proto-oncogene mutations (see, Gyllensten et al., PCR Methods and Applications, 1:91-98 (1991); U.S. Pat. No. 5,578,443, issued to Santamaria et al.; and U.S. Pat. No. 5,776,677, issued to Tsui et al.).

Various approaches to DNA sequencing exist. The dideoxy chain termination method serves as the basis for all currently available automated DNA sequencing machines, whereby labeled DNA elongation is randomly terminated within particular base groups through the incorporation of chain-terminating inhibitors (generally dideoxynucleoside triphosphates) and size-ordered by either slab gel electrophoresis or capillary electrophoresis (see, Sanger et al., *Proc. Natl. Acad. Sci.*, 74:5463-5467 (1977); Church et al., *Science*, 240:185-188 (1988); Hunkapiller et al., *Science*, 254:59-67 (1991)). Other methods include the chemical degradation method (see, Maxam et al., *Proc. Natl. Acad. Sci.*, 74:560-564 (1977), whole-genome approaches (see, Fleischmann et al., *Science*, 269:496 (1995)), expressed sequence tag sequencing (see, Velculescu et al., *Science*, 270 (1995)), array methods based on sequencing by hybridization (see, Koster et al., *Nature Biotechnology*, 14:1123 (1996)), and single molecule sequencing (SMS) (see, Jett et al., *J. Biomol. Struct. Dyn.* 7:301 (1989); Schecker et al., *Proc. SPIE-Int. Soc. Opt. Eng.* 2386:4 (1995)).

There have been several improvements in the dideoxy chain termination method since it was first reported in the mid-1980's with enhancements in the areas of separating technologies (both in hardware formats & electrophoresis media), fluorescence dye chemistry, polymerase engineering, and applications software. The emphasis on sequencing the human genome with a greatly accelerated timetable along with the introduction of capillary electrophoresis instrumentation that permitted more automation with respect to the fragment separation process allowed the required scale-up to occur without undue pressure to increase laboratory staffing. However, despite such enhancements, the reductions in the cost of delivering finished base sequence have been marginal, at best.

In general, present approaches to improve DNA sequencing technology have either involved: (1) a continued emphasis to enhance throughput while reducing costs via the dideoxy chain termination method; or (2) a paradigm shift away from the dideoxy chain termination method to alternative approaches that do not involve molecular sizing by electrophoretic means.

Although several non-sizing DNA sequencing methods have been demonstrated or proposed, all are limited by short read lengths. For example, matrix-assisted laser desorption/ionization (MALDI) mass spectrometry, which separates DNA fragments by molecular weight, is only capable of determining about 50 nucleotides of DNA sequence due to fragmentation problems associated with ionization. Other non-sizing sequencing methods depend on the cyclic addition of reagents to sequentially identify bases as they are either added or removed from the subject DNA. However, these procedures all suffer from the same problem as the classical Edman degradation method for protein sequencing, namely that synchronization among molecules decays with each cycle because of incomplete reaction at each step. As a result, current non-sizing sequencing methods are unsuitable for sequencing longer portions of DNA.

As such, there is a need for more effective and efficient methods of non-sizing DNA sequencing. The present invention satisfies this and other needs.

SUMMARY OF THE INVENTION

The present invention provides compositions, methods and apparatus for single molecule DNA sequencing that can be performed, e.g., in a two-electrode chamber such as a microtiter plate fitted with two electrodes. As such, many different single DNA molecules (e.g., over two-hundred) can be sequenced simultaneously in a single well at a rate of about 10 to about 200 nucleotides per second per molecule and at read lengths of 5-20 kilobases (kb) or more. In addition, the compositions, methods and apparatus of the present invention reduce the cost of sequencing as compared to other long read approaches due to the high degree of multiplexing and the substitution of microtiter plates for expensive micro- or nano-fabricated devices. As such, field-switch sequencing of the present invention provides long-read high-throughput sequencing with sufficient resolution for single molecule detection.

In one embodiment, the present invention provides a particle, comprising:
  a particle surface; at least one nucleotide phosphate (NP) attached to the particle surface via a linker; and
  a dye, wherein the particle carries a charge.

In certain other embodiments, the present invention provides a method for sequencing a nucleic acid, comprising:
  (a) immobilizing a plurality of complexes comprising a target nucleic acid, a primer nucleic acid, and a polymerase onto a surface;

(b) contacting the surface with a plurality of charged particles comprising a nucleotide phosphate by applying an electric field;

(c) reversing the electric field to transport unbound charged particles away from the surface; and (d) detecting the incorporation of the nucleotide phosphate into a single molecule of the primer nucleic acid.

In yet another embodiment, the present invention provides a sequencing chamber, comprising:

a first electrode on one side of the chamber;

a second electrode on another side of the chamber; and a spacer separating the first electrode and second electrode.

Other objects, features, and advantages of the present invention will be apparent to one of skill in the art from the following detailed description and figures.

BRIEF DESCRIPTION OF THE DRAWINGS

FIG. 6 A-B Panel A shows an example of random x-y coordinates for immobilized polymerases, as determined by a computer model. In the simulation, immobilized polymerases closer than 2 microns were treated as being optically unresolvable. Proteins at least 2 microns apart are marked as white squares (they can be sequenced), whereas proteins closer than 2 microns are marked as small circles (too close to sequence). The simulated results show 204 resolvable immobilized proteins among 249 total immobilized proteins. Panel B shows the total number (thin line) and resolvable number (thick line) of immobilized proteins from one simulation run. The results indicate that a maximum of about 350 resolvable proteins is achieved after about 800 total proteins have been immobilized. As the total number of protein increases above 800, the number of resolvable proteins decreases due to overcrowding.

DETAILED DESCRIPTION OF THE INVENTION

I. Definitions

Figure 1:
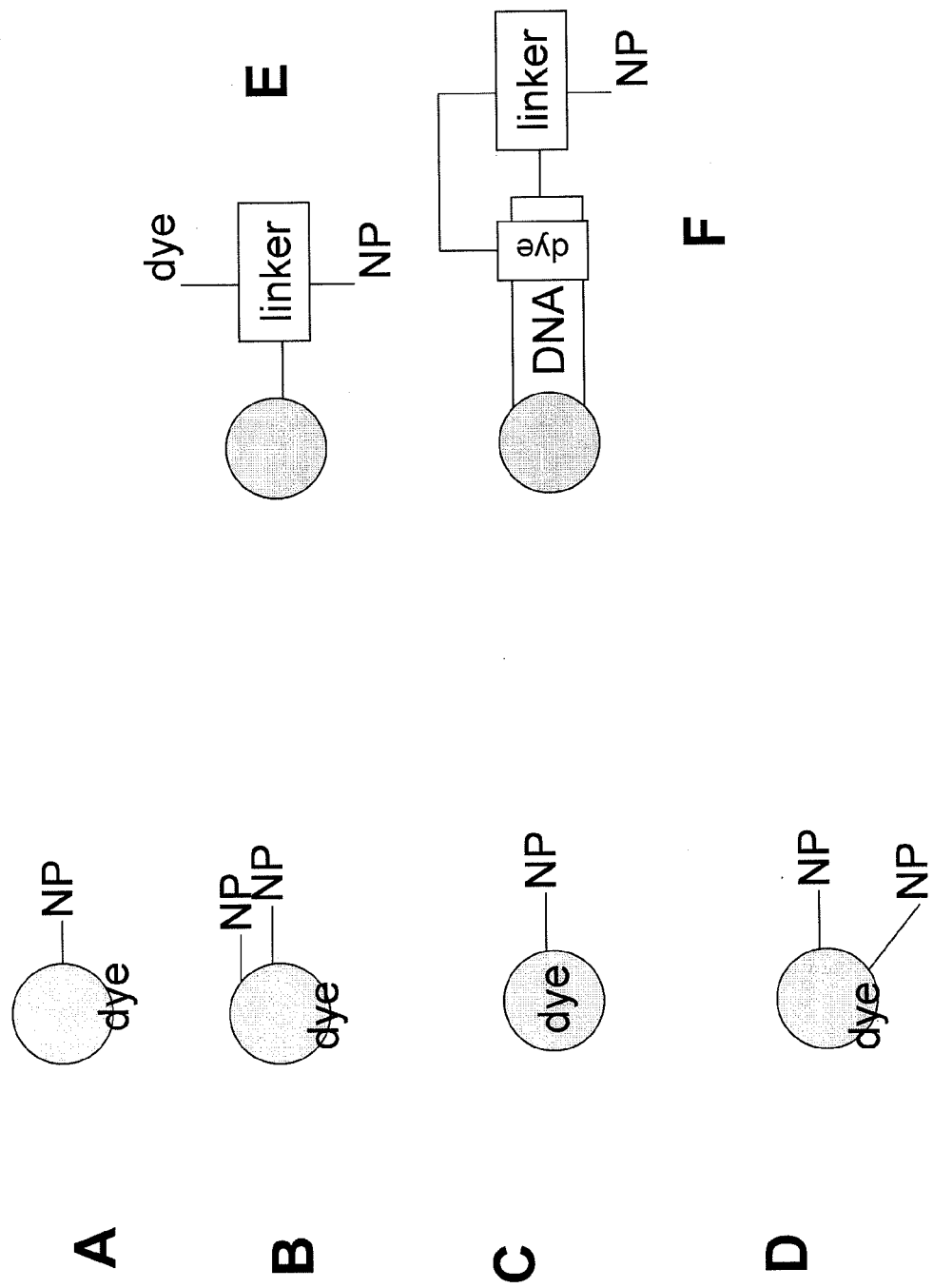
FIG. 1 A-F show various particle embodiments of the present invention. Panel A illustrates a NP attached to the particle via a linker, wherein the dye is on the surface of the particle. Panel B illustrates at least two NPs linked to a particle, wherein the dye is on the surface of particle. Panel C illustrates a NP linked to a particle, wherein the dye is embedded in the particle. Panel D illustrates a particle having a NP linked to a particle, and a dye is linked to the particle. Panel E illustrates a trifunctional linker wherein the dye, NP and particle are attached. Panel F shows a NP on one end of the linker and a dye on the other end of a linker.

As used herein, the following terms have the meanings ascribed to them unless specified otherwise.

The term "oligonucleotide" as used herein includes linear oligomers of nucleotides or analogs thereof, including deoxyribonucleosides, ribonucleosides, and the like. Typically, oligonucleotides range in size from a few monomeric units, e.g., 3-4, to several hundreds of monomeric units. Whenever an oligonucleotide is represented by a sequence of letters, it will be understood that the nucleotides are in 5'-3' order from left to right and that "A" denotes deoxyadenosine, "C" denotes deoxycytidine, "G" denotes deoxyguanosine, and "T" denotes thymidine, unless otherwise noted.

The term "nucleotide" as used herein refers to a phosphate ester of a nucleoside, e.g., mono-, di-, tri-, tetra-, penta-, hexaphosphate esters, and the like, wherein the most common site of esterification is the hydroxyl group attached to the C-5 position of the pentose. Although in many instances throughout this specification "NTP" is referred to, any of the phosphate esters (e.g., mono-, di-, tri-, tetra-, penta-, hexaphosphate esters) can be used interchangeably. Nucleosides also include, but are not limited to, synthetic nucleosides having modified base moieties and/or modified sugar moieties, e.g., described generally by Scheit, *Nucleotide Analogs*, John Wiley, N.Y. (1980). Suitable NTPs include both naturally occurring and synthetic nucleotide triphosphates, and are not limited to, ATP, dATP, CTP, dCTP, GTP, dGTP, TTP, dTTP, UTP, and dUTP. Preferably, the nucleotide triphosphates used in the methods of the present invention are selected from the group consisting of dATP, dCTP, dGTP, dTTP, dUTP, and combinations thereof.

The term "primer nucleic acid" refers to a linear oligonucleotide, which specifically anneals to a unique target nucleic acid sequence and allows for synthesis of the complement of the target nucleic acid sequence.

The phrase "target nucleic acid" refers to a nucleic acid or polynucleotide whose sequence identity or ordering or location of nucleosides is to be determined using the methods described herein.

The phrase "sequencing a nucleic acid," in reference to a target nucleic acid, includes determination of partial as well as full sequence information of the target nucleic acid. That is, the term includes sequence comparisons, fingerprinting, and like levels of information about a target nucleic acid, as well as the express identification and ordering of nucleosides, usually each nucleoside, in a target nucleic acid. The term also includes the determination of the identification, ordering, and locations of one, two, or three of the four types of nucleotides within a target nucleic acid.

The term "linker" refers to a phosphate linker moiety attached to the terminal phosphate (e.g., gamma-phosphate group of an NTP) of a nucleotide phosphate. The linker can contain carbon, oxygen, phosphorous, sulfur or hydrogen atoms. The linker is used to attach the nucleotide phosphate (e.g., NTP) to a particle directly or via a dye.

The term "unit" in reference to a nanoparticle, describes a double-stranded or single-stranded nucleic acid or analog thereof. Individual units are joined together into larger particles by attachment to a common core particle (e.g. a silica nanoparticle), by attachment to each other by complementary base pairing or covalent linking, or by being arrayed along a single strand as tandem direct repeat or inverted repeat sequences.

The term "haripin unit" is a single-strand inverted repeat sequence capable of self-hybridizing into a single stem-loop structure or into multiple stem-loops. Base pairing along the double-stranded stems may be either perfectly complementary or may contain mismatches.

II. Overview

In certain aspects, the present invention provides methods, compositions and apparatus for field-switch sequencing, wherein nucleotide phosphates (e.g., NTPs) such as deoxyribonucleotide triphosphates (e.g., dNTPs) are attached to nanoparticles. In one embodiment, the terminal phosphate (e.g., γ-phosphate group of a NTP) is tethered via a linker to the surface of the nanoparticle. In a preferred embodiment, the linker comprises polyethylene glycol (PEG) attached to for example, a trifunctional group for connecting together the dye, the nucleotide and the particle. In another preferred embodiment, the NTP is first linked to a dye, and the NTP-dye compound is then attached to a particle. In certain instances, several hundred NTP-dyes are coupled to the surface of a nanoparticle; for example, given 100% coupling efficiency between a NTP-dye and an amino-DNA, a particle comprising 18 haripin units, wherein each unit contains 17 amino-modified bases, has 17×18=306 NTP-dyes. Exceptionally bright fluorescence from these nanoparticles enables a charged-couple device (CCD) camera to image about 200-300 individual optically-resolved particles simultaneously with millisecond exposure times. In addition to improved detectability, the nanoparticles are also capable of carrying a substantial electric charge. In certain preferred instances, fluorescence and electric charge are elements of the field-switch sequencing particles of the present invention.

III. Nanoparticles

Advantageously, the particles of the present invention are used to carry or transport the substrate nucleotide phosphates (NPs) to a polymerase (e.g., immobilized polymerase). Each particle has at least one NP, preferably at least two NPs and more preferably a plurality of NPs associated therewith. Preferably, the NP is attached to the particle via a linker. In certain instances, the present invention provides a particle, comprising: a particle surface; at least one nucleotide phosphate attached to the particle surface via a linker; and a dye, wherein the particle carries a charge.

The nucleotide phosphate is for example, a nucleotide diphosphate, a nucleotide triphosphate (NTP), a nucleotide tetraphosphate, a nucleotide pentaphosphate or a nucleotide hexaphosphate. Preferably, a nucleotide phosphate is a nucleotide triphosphate such a NTP or dNTP.

In certain instances, a label (e.g., a fluorescent dye, a mass tag, a chromogenic labels, and the like) is associated with the particle. Preferably, the label or dye is associate or attached to the surface of the particle. In other aspects, the dye is embedded in the particle. In still other preferred aspects, the dye is attached to one end of the linker, wherein the NP is attached to the other end of the linker.

FIG. 1 illustrates various embodiments of the particles of the present invention. FIG. 1A illustrates a NP attached to the particle via a linker, and wherein the dye is on the surface of the particle. FIG. 1B illustrates at least two NPs linked to a particle, wherein the dye is on the surface of particle. FIG. 1C illustrates a NP linked to a particle, wherein the dye is embedded in the particle. FIG. 1D illustrates a particle having a NP linked to a particle, and a dye is linked to the particle. FIG. 1E illustrates a trifunctional linker wherein the dye, NP and particle are attached via a linker. FIG. 1F shows a NP on one end of the linker and a dye on the other end of a linker. The dye intercalates into the nucleic acid nanoparticle. In certain embodiments, a linker connects the terminal phosphate of the NP to the particle, and a second linker connects the dye to the particle. Preferred linkers comprise backbone chains of carbon, nitrogen, oxygen, sulfur, phosphorus and combinations thereof. In another embodiment, a the NP linker and the dye linker are connected to a common linker, and the common linker is connected to the particle. In a preferred embodiment, the common linker is a trifunctional moiety, for example an amino acid having an amino group, a carboxylate group and a side-chain functional group. In a most preferred embodiment, the common linker is cysteine, aspartate, glutamate or lysine.

A wide variety of particles are suitable for the present invention. These particles include, but are not limited to, a nucleic acid nanoparticle, a nucleic acid analog particle, a semiconductor nanoparticle, a nanocrystal, a silicon nanocrystal, a metallic nanoparticle, a silica-shell nanoparticle, a dye-doped silica-shell nanoparticle, a nanoparticle made of an organic polymer, a dendrimer, a light-scattering nanoparticle, an electroactive nanoparticle, a coated nanoparticle, a lipid nanoparticle, a protein nanoparticle, a fluorescent protein, and combinations thereof. In certain preferred aspects, the particle is a nucleic acid nanoparticle.

Various nucleic acid nanoparticles are useful in the present invention. These nucleic acid nanoparticles include, but are not limited to, a hairpin structure consisting of tandem inverted repeat DNA sequences, a DNA nanoparticle, a RNA nanoparticle, a silica-DNA nanoparticle, a nucleic acid analog nanoparticle, a DNA nanoparticle comprising multiple complementary and non-complementary strands of single stranded DNA, an RNA nanoparticle comprising multiple complementary and non-complementary strands of single stranded RNA, and a combination thereof. Preferably, the nucleic acid particle is a hairpin structure consisting of tandem inverted repeat DNA sequences.

Figure 2:
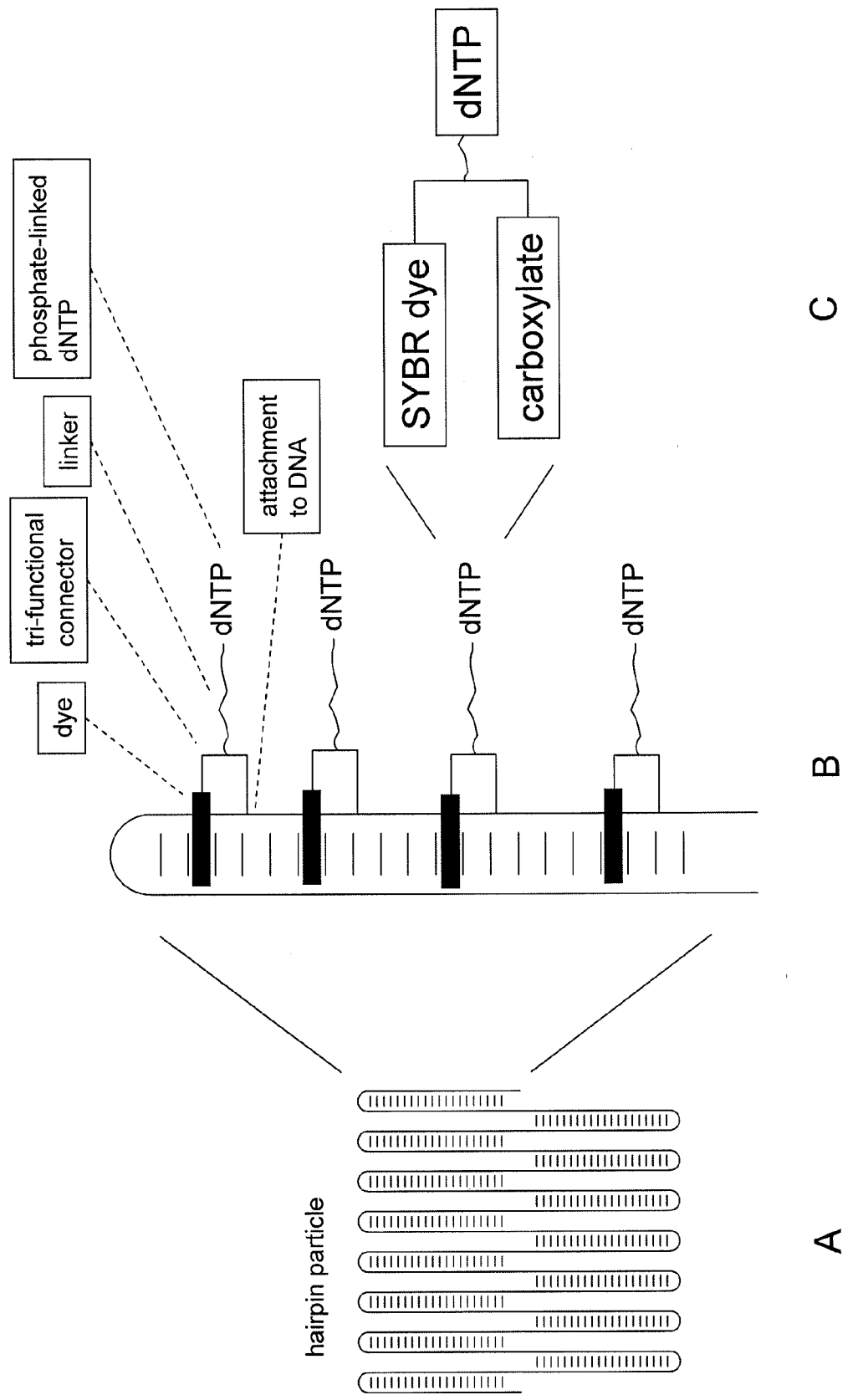
FIG. 2 shows a nucleic acid nanoparticle configuration of the present invention Panel A shows a particle comprising multiple hairpin structures. Panel B shows a single hairpin unit (U-shaped line; basepairs schematically indicated by horizontal line pattern) with 4 intercalated, covalently attached SYBR dyes (black rectangles). Panel C shows an example connector with carboxylate functionality for conjugation to amino-modified bases on the DNA.

FIG. 2 shows a nucleic acid nanoparticle configuration of the present invention. As shown therein, a SYBR-dNTP is intercalated into and covalently attached to, double-stranded DNA comprising a hairpin-type particle. Panel A shows a particle comprising multiple hairpin structures formed from tandem inverted repeat sequences along a single strand. Panel B shows a single hairpin unit W-shaped line; basepairs schematically indicated by horizontal line pattern) with 4 intercalated, covalently attached SYBR dyes (black rectangles). A tri-functional connector such as an amino acid residue, joins the dye both to the DNA and to a phosphate-linked dNTP. Panel C is an example of a trifunctional connector with carboxylate functionality for conjugation to an amino-modified bases on the DNA.

In certain embodiments, other particle types are suitable for use in the present invention. These particles include, but are not limited to, 20 nm polystyrene spheres (Molecular Probes); semiconductor nanocrystals (Quantum Dot Corporation); RLS metal particles (Invitrogen); dye-doped silica shell nanoparticles; silicon crystal nanoparticles; and DNA dendrimers (Genisphere)). In certain other aspects, nanoparticles made of DNA are useful (Tapec et al., *J. Nanosci. Nanotechnol.*, 2:405 (2002); Belomoin et al., *App. Phys. Lett.*, 80:841 (2002)). In certain aspects, DNA intercalating dyes from Molecular Probes (e.g., YOYO, JOJO, BOBO, POPO, TOTO, LOLO, SYBR, SYTO, SYTOX, PicoGreen, OliGreen etc.) are useful to intercalate the linker having the NP attached thereto with the particle. As a result, particles containing a plurality dyes (e.g., several hundred) are bright enough for millisecond detection by a CCD camera. DNA provides a structured environment that allows intercalating dyes to pack densely (e.g., 1 dye:10 base pairs) into nanoscale volumes without being quenched. In fact, fluorescence is enhanced several hundred-fold upon intercalation. In addition to high dye density, DNA particles naturally provide: 1) high charge density; 2) facile self-assembly of defined structures; and 3) a flexible particle surface for improved thermal motion of surface-attached dNTPs. Moreover, dye intercalation stabilizes the double helix, as evidenced by increasing the $T_m$ from 65° C. to 95° C. upon intercalation of 6 YOYO dyes into a 30-mer dsDNA oligonucleotide (Bjorndal et al., *Biopolymers*, 65:40 (2002)).

In certain embodiments, the particle surface comprises a functional group. The functional group can be a reactive functional group. Suitable functional groups include, but are not limited to, a haloacetyl group, an amine, a thiol, a phosphate, a carboxylate, a hydrazine, a hydrazide an aldehyde or a combination thereof. Other functional groups include groups such as a reactive functionality (A) or a complementary group (B) set forth in Table I below.

Preferably, the at least one nucleotide phosphate such as a dNTP is attached to the particle surface via a linker. The linker is a combination of atoms having stable chemical bonds, and optionally includes single, double, triple, aromatic carbon-carbon bonds, as well as carbon-nitrogen bonds, nitrogen-nitrogen bonds, carbon-oxygen bonds and carbon-sulfur bonds. The linker typically includes ether, thioether, carboxamide, sulfonamide, urea, urethane or hydrazine moieties. Preferably, the linker has 1-50 nonhydrogen atoms selected from the group of C, N, O and S; and are composed of any combination of ether, thioether, amine, ester, carboxamide, sulfonamide, hydrazide bonds and aromatic or heteroaromatic bonds. Preferably, the linker is a combination of single carbon-carbon bonds and carboxamide or ether bonds. Examples of the linker include substituted or unsubstituted polymethylene, arylene, alkylarylene or arylenealkyl.

In a preferred embodiment, the linker is an aliphatic chain containing a backbone of 4-50 carbon atoms. The carbon backbone may be interspersed at one or more intervals with a non-carbon heteroatom. The heteroatoms, which may be the same or different are N, O, or S. Where the heteroatom is nitrogen, it is optionally substituted with one or more alkyl substituents having 1-6 carbon atoms, which may be the same or different. In certain aspects, the linker incorporates quaternary nitrogens, which confer cationic charges on the particles of the invention.

In certain preferred aspects, the linker is a polyethylene glycol (PEG) linker. The PEG linker is a —(OCH$_2$CH$_2$)$_n$— polymer, wherein n is about 1-50, preferably about 4-30 and more preferably about 6-20. The linker attaches to the nucleotide phosphate on one end, and a dye on the other end. The attachment of the linker to the nucleotide phosphate is via complementary functional groups. Similarly, the attachment of the linker to a dye is via complementary functional groups. In another aspect, the linker can be attached directly to the particle without an intervening dye. In a preferred embodiment, both the dye and the NTP are covalently attached to the particle. For example, the dye and NTP are covalently attached via a linker (bi- or trifunctional) to form a dye-NTP moiety, and the dye-NTP moiety is covalently attached to the particle.

Selected examples of reactive functionalities useful for the attaching the linker to the nucleotide phosphate and the linker to a dye or the linker directly to the particle surface are shown in Table I, wherein the bond "C" results from such a reaction. Those of skill in the art will know of other bonds suitable for use in the present invention.

TABLE I

| Reactive functionality (A) | Complementary group (B) | The resulting bond (C) |
|---|---|---|
| activated esters | amines/anilines | carboxamides |
| acrylamides | thiols | thioethers |
| acyl azides | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides/imides |
| aryl halides | thiols | thiophenols |
| aryl halides | amines | aryl amines |
| aziridines | thiols | thioethers |
| boronates | glycols | boronate esters |
| carboxylic acids | amines/anilines | carboxamides |
| carboxylic acids | alcohols | esters |
| carboxylic acids | hydrazines | hydrazides |
| carbodiimides | carboxylic acids | N-acylureas or anhydrides |
| diazoalkanes | carboxylic acids | esters |
| epoxides | thiols (amines) | thioethers (alkyl amines) |
| epoxides | carboxylic acids | esters |
| haloacetamides | thiols | thioethers |
| haloplatinate | amino | platinum complex |
| haloplatinate | heterocycle | platinum complex |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonyl halides | amines/anilines | sulfonamides |

In still other embodiments, the particle can further comprise an oligonucleotide or a plurality of oligonucleotides. Due to the highly negatively charged groups, in certain instances, the oligonucleotide imparts a negative charge onto the particle. In other instance, the oligonucleotide can be used as an appendage to attach other moieties for example, attach a dye or an NP (e.g., NTP), to the particle. The NTP can be attached to the oligonucleotides via covalent bonding, non-covalent bonding, via ionic bonding, hydrophobic interactions or a combination thereof.

In another aspect, the particle can be used as a scaffold to attach analytes for example, small molecules (e.g., LIGANDS), for specific interactions with nucleic acids, carbohydrates, lipids, proteins, antibodies, or other ligand binders (TARGETS) bound to the chamber surface. In yet another embodiment, ligands can be attached to the chamber surface and targets can be attached to the particles. Ligands and targets can be attached to particles or the chamber surface by covalent bonding, non-covalent bonding, via ionic bonding, hydrophobic interactions or a combination thereof.

A wide variety of dyes are suitable for use in the present invention. The dye can be associated or attached to the surface of the particle. In other aspects, the dye is embedded into the particle. In still other aspects, the dye is attached to one end of the linker, wherein the NP is associated or attached to the other end of the linker. The dye is preferably a fluorescent dye, or a plurality of fluorescent dyes. Suitable dyes include, but are not limited to, YOYO-1, JOJO-1, LOLO-1, YOYO-3, TOTO, BOBO-3, SYBR, SYTO, SYTOX, PicoGreen, Oli-Green, and combinations thereof. Other dyes include, thiazole orange, oxazole yellow, or non-intercalating dyes such as fluorescein, rhodamine, cyanine or coumarin based dyes, and combinations thereof. The dye can be an intercalating dye or a nonintercalating dye. In certain instances, the dye molecules are attached to a plurality of oligonucleotides via covalent bonding. In certain other instances, the dye molecules are attached to the plurality of oligonucleotides via ionic bonding.

Other suitable dyes include, but are not limited to, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives: coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5',5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM), 5-(4,6-dichlorotriazin-2-yl)aminofluorescein (DTAF), 2',7'-dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Ciba-cron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid; terbium chelate derivatives; Cy 3; Cy 5; Cy 5.5; Cy 7; IRD 700; IRD 800; La Jolla Blue; phthalocyanine; and naphthalo cyanine.

A wide variety of particles sizes are suitable for the present invention. In certain aspects, the particle has a diameter of about 10 nanometers to about 10 microns. Preferably the particle diameter is about 20 to 700 nanometers, and more preferably, the diameter of about 20 nanometers to about 100 nanometers (e.g., 55 nm)

Detection of the dye labeled particle of the present invention can be performed using a variety of systems and/or devices. Suitable systems and devices include, but are not limited to, an optical reader, a high-efficiency photon detection system, a photodiode, a camera, a charge couple device, an intensified charge couple device, an on-chip multiplication gain charge coupled device, a near-field scanning microscope, a far-field confocal microscope, a microscope that detects wide-field epi-illumination, and a total internal reflection fluorescence microscope.

In certain preferred aspects, the detection device is a total internal reflection fluorescent microscope, using for example, either evanescent wave excitation or surface plasmon excitation. A catalytic event can be detected by one or more cleavage molecules, or while the nucleotide phosphate is resident with the polymerase. In a preferred embodiment, the methods described herein detect the "residence time," or a "resident event" of a nucleotide phosphate on a polymerase, such as within the active site. In certain instances, polymerase catalyzed nucleotide incorporation is synchronized with the application of an electric field. Preferably, detection is carried out by a mechanism that provides low background and enables the detection of single molecules. Various mechanism can be used for example, fluorescence resonance energy transfer, an electron transfer mechanism, an excited-state lifetime mechanism and a ground-state complex quenching mechanism.

In one embodiment, the detection device is a four color single molecule imaging microscope with total internal reflectance (e.g., evanescent wave) excitation and a CCD camera to image a field of view (e.g., a 100 μm×100 μm field of view). The camera is, e.g., a Micromax 512×512 or a Pentamax intensified CCD from Roper Scientific. The mean background noise with the laser on is 10 electrons. With 2×2 pixel binning and a 2 MHz readout, the total frame readout time is 33 msec, which is compatible with a 100 msec field-switch sequencing cycle. Single immobilized TAMRA molecules are typically imaged in 80 msec with an SN of ~11.

Figure 3:
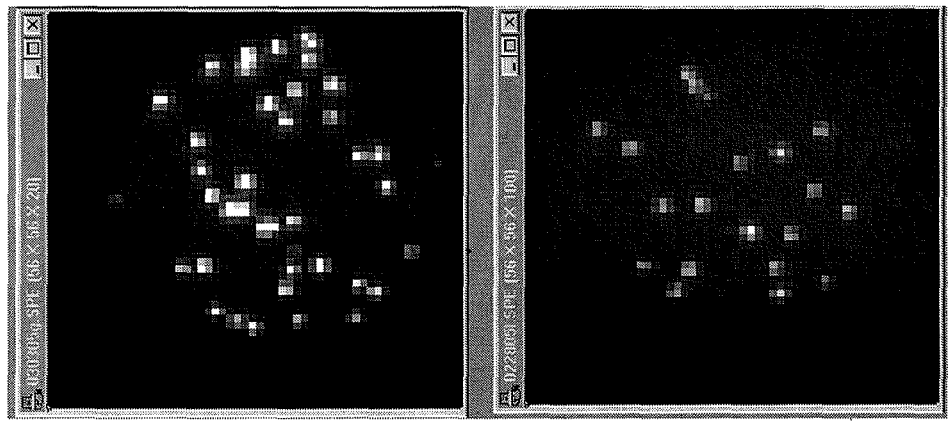
FIG. 3 shows a DNA particle (a 2.7-kb pUC plasmid) stained with ~300 molecules each of YOYO-1 or TOTO-1. Samples (1 million particles per uL) were adsorbed to poly-L-lysine coated glass coverslips and the DNA was imaged by objective-type TIR. Excitation power was 1 mW spread over a 100 um diameter spot. Laser wavelengths were: YOYO-1 at 488 nm, TOTO-1 at 514 nm and TOTO-3 at 647 nm. Exposures were 2 msec using a Roper MicroMax 512 CCD camera, and pixel binning was set to 9×9. Signals are indicated for selected particles. Signal to noise (SN) was calculated as the ratio (S−B)/stdev, where S=the integrated signal of a single particle, B=average background, stdev=standard deviation of background pixels.

In certain preferred aspects, the staining of DNA with an intercalating dye give sufficient SN for a nano-scale particle. For example, as shown in FIG. 3, 2.7 kb DNA fragments containing about 300 YOYO-1 or TOTO-1 dye molecules were imaged in 2 msec with SN 186 and 75, respectively. This SN is more than sufficient for unambiguous detection of the particles.

In a further embodiment, a frame transfer CCD is used to capture images (Roper Micromax, I-Pentamax, Cascade). These cameras are capable of a short 1 msec exposure followed by a 40 msec readout. This timing is compatible with the field-switch cycle. Since these cameras are capable of acquiring two images in rapid succession (spaced by 1 msec) followed by an 80 msec readout, two images per cycle are acquired. In one aspect, four color detection is accomplished by a dichroic image splitter (Roper Scientific) mounted in front of a camera.

In certain other instances, one or more dyes or used, in other instances, two or more dyes or used, in other instances, three or more dyes or used and in still other instances, four or more dyes or used. In one embodiment, two dyes are mixed in 4 different ratios within the particles in order to provide 4 different fluorescence signatures (i.e. "colors") using only two dyes. In general, it is not necessary to associate a different dye with each NTP type; rather, two or more dyes can be used in unique dye mixtures to produce the required number of fluorescence signatures. While it is preferred for sequencing to associate a unique fluorescence signature with each nucleotide type attached to the particle, in some applications, 2 or more nucleotide types are attached to the same particle, or different particles having the same fluorescence signature. In yet other embodiments, additional binding moieties are attached to the particles in order to enhance binding between the polymerase and the particle.

Suitable dyes for use in the nanoparticles of the present invention include, without limitation, a family of homodimeric cyanine DNA intercalating dyes from Molecular Probes that cover the visible spectrum, such as YOYO-1 (488/509), JOJO-1 (532/545), LOLO-1 (565/579), and YOYO-3 (612/631), SYBR-101 (488/505) and SYTO-62 (652/676). Given sufficient detection SN, dyes are mixed in various ratios in a single particle such that, for example, different fluorescence spectra are obtained from mixtures of just 2 dyes. In monitoring the fluorescence of individual stained DNA molecules (JOJO-1) over time, an exponential photobleaching decay constant of $8 \times 10^4$ msec$^{-1}$ was determined, meaning that fluorescence decreases 8 parts per 10,000 for each msec of exposure to the excitation laser beam (2.7 W/cm$^2$). Particles are preferably illuminated while trapped by a polymerase, and detected.

IV. Field Switch Sequencing Methods

In certain embodiments, the present invention provides a method for sequencing a nucleic acid, comprising:

(a) immobilizing a plurality of complexes comprising a target nucleic acid, a primer nucleic acid, and a polymerase onto a surface;

(b) contacting the surface with a plurality of charged particles comprising a nucleotide phosphate by applying an electric field;

(c) reversing the electric field to transport unbound charged particles away from the surface; and (d) detecting the incorporation of the nucleotide phosphate into a single molecule of the primer nucleic acid.

Figure 4:
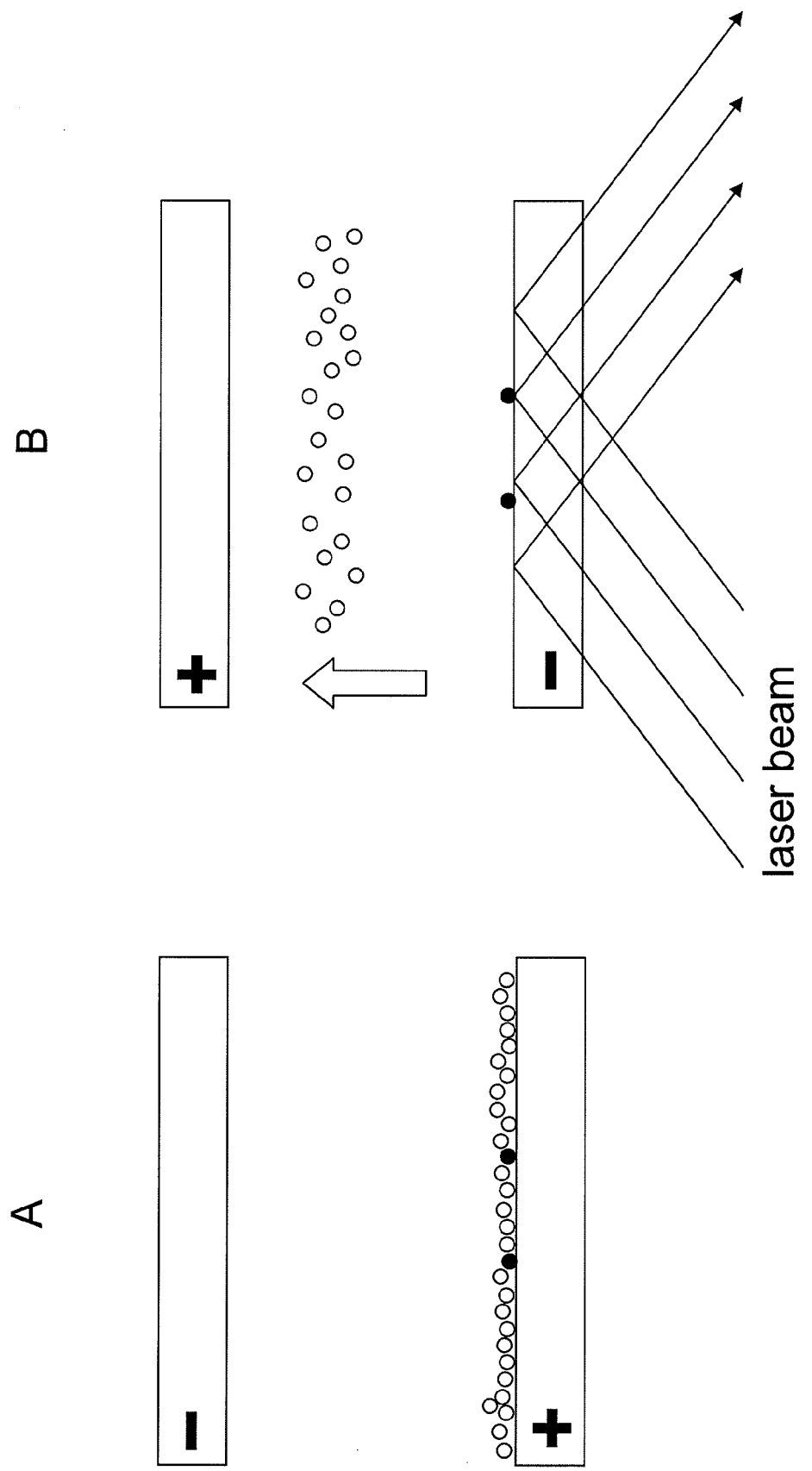
FIG. 4 shows an cycle in the field-switch sequencing method of the present invention. Panel A illustrates the accumulation of negatively-charged particles (white and black circles) above immobilized polymerase-DNA complexes on a positively-charged indium-tin oxide (ITO) electrode (bottom rectangle). Particles bound by polymerases are shown (black circles). Panel B illustrates the movement of unbound particles away from the ITO electrode when the electric field is reversed. The ITO electrode surface is illuminated by total internal reflection (arrows) and the particles retained by the polymerase-DNA complexes are imaged without interference from unbound particles which have moved away from the surface FIG. 5 A-B Panel A shows a diagram of a circular template that is permanently associated with the anchored polymerase, while still being able to slide through the DNA binding groove to permit primer extension. The tunnel formed by polymerase immobilization is roughly the same dimension as a DNA sliding clamp. Panel B shows the structure of a polymerase. The template strand feeds into the DNA binding cleft between the biotin loops (SEQ ID NO:1), trapping it between the enzyme and the immobilization surface. The primer strand, which is extended at its 3'-end by polymerization of dNTPs, exits the polymerase with the template strand as shown.

In certain aspects, the field-switch sequencing methods of the present invention comprise cycled transport of nanoparticle nucleotides between a bottom electrode and a top electrode (FIG. 4). In one embodiment, the bottom electrode is the glass bottom of a microtiter well coated with electrically-conductive, optically-transparent indium-tin oxide (ITO). In one aspect, about 2 to 1000, preferably 50 to 700, more preferably 200-300 polymerase-DNA complexes are immobilized in the field of view at random positions on the bottom of a well, such that the majority of complexes are optically resolvable from their nearest neighbors. This allows many different molecules (e.g., about 200-300) to be sequenced simultaneously by imaging with a CCD camera (e.g., a 100 μm field).

In certain preferred aspects, the sequencing cycle comprises a wave of charged particles, which is cycled between electrodes by an alternating electric field (E-field). First, charged particles (e.g., anions) are concentrated at the bottom electrode to blanket the immobilized polymerase-DNA complexes. This allows polymerases to bind the correct nucleotides for incorporation into DNA. Next, the E-field is reversed to transport unbound particles away from the surface, leaving only particles retained by the polymerases. With unbound particles now cleared from the surface (e.g., a 200-800 nm distance is sufficient), retained particles are imaged by for example, evanescent wave or surface plasmon excitation with millisecond time resolution while the catalytic reaction is in progress.

FIG. 4 shows an cycle in the field-switch sequencing method of the present invention. With reference to panel A, it is shown that negatively-charged particles (white and black circles) accumulate above immobilized polymerase-DNA complexes on a positively-charged indium-tin oxide (ITO) electrode (bottom rectangle). Particles bound by polymerases are shown (black circles). After the E-field is reversed, FIG. 4 panel B illustrates the movement of unbound particles away from the electrode. The electrode surface is illuminated by total internal reflection (arrows) and the particles retained by the polymerase-DNA complexes are imaged without interference from unbound particles which have moved away from the surface. Each particle comprises at least 1 NP, or at least two NPs, or a plurality of NPs.

In certain aspects, images are acquired before the catalytic reaction is completed because, after incorporation of the nucleotide into DNA, the terminal phosphate (e.g., pyrophosphate) and the attached nanoparticle are released from the enzyme. This completes one sequencing cycle. The timing of E-field switching and image acquisition is dictated by the duration of the catalytic cycle, and ranges from about 1 msec to 1 sec (e.g., 1 msec-100 msec) (see, Levene et al., *Science*, 299:682 (2003)). In certain aspects, the detecting comprises detecting one or more cleavage molecules, either before, during or after the E-field is reversed. In other instances, the detecting comprises detecting the nucleotide phosphate (e.g., dNTP) while associated with the polymerase.

In certain other aspects, sequencing is performed with only 1 image per cycle, taken as soon as the free particles are transported away from the surface. In a preferred embodiment, a second image is taken at the end of each cycle to identify any "background" particles still bound to the electrode. In yet another embodiment, multiple images are taken during each cycle to monitor the release time of individual particles bound to the immobilized polymerases. High nucleotide surface density, flexible tethered nucleotides, and high particle concentrations at the electrode all have positive effects on polymerase binding kinetics.

In one embodiment, when the field-switch cycle operates at about 10 cycles/sec (i.e., 100 msec period), the sequencing speed is about 10 bases per second. At this speed, a 20 kb DNA molecule is sequenced in about 33 min. In addition, net throughput is significantly enhanced by multiplexing. For example, with an average of one polymerase-DNA complex per 50 $\mu m^2$ area, there are about 200 optically-resolved complexes in the optical field (100×100 $\mu m$) on the imaged electrode surface. In this embodiment, each well is used once for a period of 33 min. to simultaneously sequence all 200 20 kb DNA molecules (i.e., 4 million bases total). Then, the next 4 million bases are sequenced at a new region of the electrode, and so on. Although it takes about 30-40 days to process an electrode with 1536 individual observation areas, one observation area at a time, the plate is processed 4 times faster (i.e., in 7-10 days) by quadruplexing the instrument optics. Under these conditions, a 1536 well microtiter plate (i.e. one observation area per microtiter well) produces the equivalent of 2 human genomes worth of sequence (i.e., 4 million bases/well×1536 wells=6.1 billion bases total).

A. Topologically Linked Polymerase-DNA Complexes

In a preferred embodiment, the polymerase-DNA complexes are taught and described in U.S. Patent Publication No. 2005/0042633, published Feb. 24, 2005, and incorporated herein by reference. As described therein, a polymerase-nucleic acid complex (PNAC), comprises: a target nucleic acid and a nucleic acid polymerase, wherein the polymerase has an attachment complex comprising at least one anchor, which at least one anchor irreversibly associates the target nucleic acid with the polymerase to increase the processivity index. As used herein, the term "processivity index" means the number of nucleotides incorporated before the polymerase dissociates from the DNA. Processivity refers to the ability of the enzyme to catalyze many different reactions without releasing its substrate. That is, the number of phosphodiester bonds formed is greatly increased as the substrate is associated with polymerase via an anchor.

Figure 5:
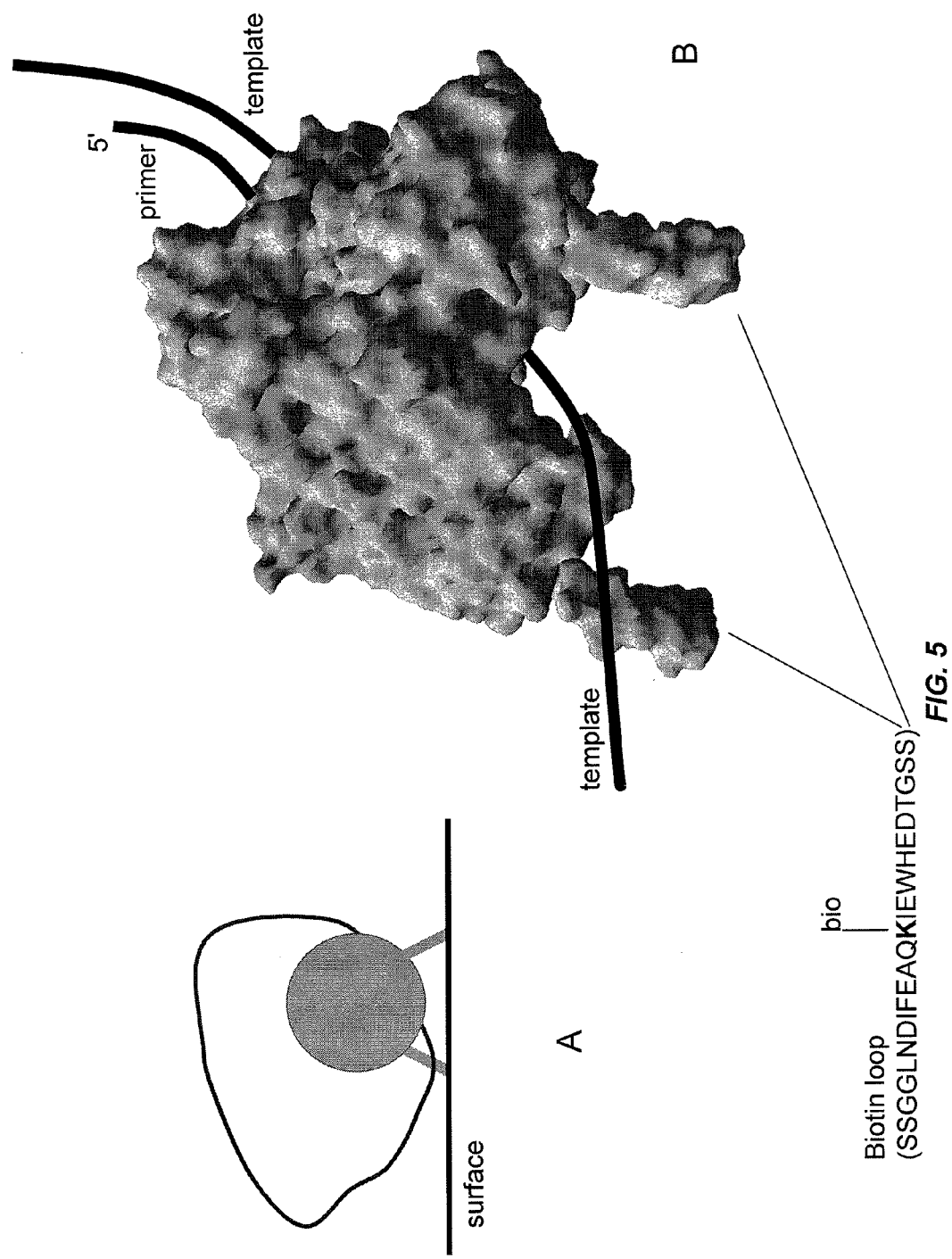

In a preferred embodiment, the polymerase is attached to the ITO permeation layer and stably associated with a DNA template to achieve long sequence reads. The polymerase can be attached to the ITO permeation layer via various linkages including, but not limited to, covalent, ionic, hydrogen bonding, Van der Waals' forces, and mechanical bonding. Preferably, the linkage is a strong non-covalent interaction (e.g. avidin-biotin) or is covalent. In order to permanently associate the DNA template and the polymerase to the ITO permeation layer, an approach that functionally mimics the sliding clamp of a replisome, as described in Shamoo et al., *Cell*, 99:155 (1999), can be used. As shown in FIG. 5, the polymerase-DNA complex is attached to the ITO permeation layer through two biotin modifications on the polymerase binding to streptavidin covalently linked to the permeation layer. This topology irreversibly captures the DNA while still allowing it to slide through the polymerase active site. Circular in form, the DNA (~20 kb) is topologically linked to the immobilized polymerase, and therefore does not dissociate.

B. Polymerases

In certain instances, the methods of the present invention employ a DNA polymerase such as DNA polymerase I, II, or III. In certain other instances, suitable polymerases include, but are not limited to, a DNA-dependent RNA polymerase and reverse transcriptase such as an HIV reverse transcriptase. Specific examples include, but are not limited to, T7 DNA polymerase, φ29 DNA polymerase, T5 DNA polymerase, *E. Coli* DNA polymerase I, T4 DNA polymerase, T7 RNA polymerase, Taq DNA polymerase, Vent DNA polymerase and Terminator polymerase. Those of skill in the art will know of other enzymes or polymerases suitable for use in the present invention.

In certain aspects, the polymerases useful in the present invention are selected from the A family polymerases or the B family polymerases. DNA-dependent DNA polymerases have been grouped into families, including A, B, X, and others on the basis of sequence similarities. Members of family A, which includes bacterial and bacteriophage polymerases, share significant similarity to *E. coli* polymerase I; hence family A is also known as the pol I family. The bacterial polymerases also contain an exonuclease activity, which is coded for in the N-terminal portion. Family A polymerases include for example, Klenow, Taq, and T7 polymerases. Family B polymerases include for example, the Terminator polymerase, phi29, RB-69 and T4 polymerases.

In certain instances, suitable DNA polymerases can be modified for use in the present invention. These polymerases include, but are not limited to, DNA polymerases from organisms such as *Thermus flavus, Pyrococcus furiosus, Thermotoga neapolitana, Thermococcus litoralis, Sulfolobus solfataricus, Thermatoga maritima, E. coli* phage T5, and *E. coli* phage T4. The DNA polymerases may be thermostable or not thermostable.

In other embodiments, the polymerases include T7 DNA polymerase, T5 DNA polymerase, HIV reverse transcriptase, *E. coli* DNA pol I, T4 DNA polymerase, T7 RNA polymerase, Taq DNA polymerase and *E. coli* RNA polymerase. In certain instances, exonuclease-defective versions of these polymerases are preferred. The efficiency with which γ-labeled NTPs are incorporated may vary between polymerases; HIV-1 RT and *E. coli* RNA polymerase reportedly readily incorporate γ-labeled nucleotide. The polymerase can also be a T7 polymerase. T7 polymerase has a known 3D structure and is known to be processive. In order to operate in a strand-displacement mode, the polymerase requires a complex of three proteins: T7 polymerase+thioredoxin+primase (Chowdhury et al. PNAS 97:12469). In other embodiments, the polymerases can also be HIV RT and DNA Polymerase I.

For Therminator polymerase, protein regions on either side of the DNA binding cleft likely to be conformationally rigid were identified based upon previous studies with RB69 polymerase. Loops of ten amino acids containing a 6×His sequence at five candidate positions were inserted. Loops inserted at positions K53 and K229 had no deleterious effect on polymerase activity when present either individually or combined.

Suitable covalent coupling methods include, without limitation, a maleimide or thiol-activated permeation layer coupled to specific cysteine amino acids on the polymerase surface, a carboxylate permeation layer coupled to specific lysine amino acids on the polymerase surface, a hydrazine permeation layer coupled to the unnatural amino acid p-acetyl-L-phenylalanine on the polymerase surface, and the like. The latter is particularly useful because of its high coupling specificity, and long reactant shelf life. Given a suitable coupling chemistry, complexes are formed by mixing the polymerase with primed circular DNA and driving them electrically to the electrode surface for covalent coupling. To ensure that most anchored proteins are associated with template, DNA is used at concentrations exceeding the binding constant. Polymerases anchored without DNA are neglected because they have no sequencing activity. In certain aspects, when polymerase attachment is complete, the electric field is reversed to elute linear (e.g., broken) DNA templates, such that the only anchored polymerases capable of generating sequence data are those complexed with circular DNA templates. As shown in FIG. 6A, a simple computer model indicates that polymerase-DNA complexes (e.g., 200-300) can be dispersed randomly in a field (e.g. a 100 μm) of view at optically resolvable distances. In certain preferred aspects, polymerase-DNA complexes being optically resolvable is an important feature of the present invention. The number of resolvable complexes decreases at higher densities (FIG. 6B) because of overcrowding. Random dispersion on a surface (e.g., ITO) provides an easy way to isolate single molecules for multiplexed, long-read sequence analysis. In some aspects, polymerase-DNA complexes can be attached in random orientation to the electrode by either covalent or non-covalent interactions; polymerases attached in active orientations are functional for sequencing.

V. Field-Switch Cycle and Electrode Design

In one embodiment, the present invention provides an integration of electrophoretic particle control with an ITO electrode and total internal reflection (TIR) optics for field-switch sequencing. This type of setup has been used, e.g., to accelerate antibody-antigen binding kinetics and confine fluorescence detection to the electrode surface (Asanov et al., *Anal. Chem.*, 70:1156 (1998); Liron et al., *Biosens. Bioelectron.*, 17:489 (2002)). Electrophoretic control has been used (to control hybridization kinetics on DNA chips operating both with faradaic current (Sethi et al., *Clin. Chem.*, 50:443 (2004)) and non-faradaic (capacitive) current (Heaton et al., *Proc. Natl. Acad. Sci. USA* 98:3701 (2001)). Ultrasensitive fluorescence detection has been demonstrated on ITO electrodes by imaging single dye molecules with TIR optics (Lu et al., *J. Phys. Chem. B.*, 101:2753 (1997)).

Table II shows an example of a field-switch cycle, in which particle transport times were determined by simulation with the computer model described above. In a preliminary step, particles are transported (10 μm) from the top electrode to the ITO electrode ("ITO") in 2.4 msec (step #1). Due to a small amount of diffusive broadening in transit, particles accumulate at the ITO over a period of ~0.1 msec. Time-critical steps immediately follow, with initiation of polymerase binding marking the start of a new cycle: $t_o$=0.0 msec (step #2). At t=0.3 msec, the electric field is reversed to transport particles away from the ITO (step #3). The surface is imaged as soon as unbound particles have cleared the evanescent zone: t=0.6 msec (step #4). At 2.8 msec, the particles have accumulated at the top electrode (step #5), where they are held (step #6) until needed for the next cycle (repeat from step #1). In this 100 msec cycle, particles spend ~95 msec idle at the top electrode to allow all polymerases to complete their respective catalytic cycles. To maintain electrochemical balance, the electric field alternated rapidly (e.g., 1-10 kHz) at reduced voltages.

TABLE II

The Field-switch Cycle of 55 nm Particles at 1 pN Particle Force.

| Step | Start (msec) | Finish (msec) | Particle Position | Image |
|---|---|---|---|---|
| 1 | −2.4 | 0 | Transit to ITO | |
| 2 | 0.0 | 0.3 | Polymerase binding at ITO surface | |
| 3 | 0.3 | 0.6 | Transit to top | |
| 4 | 0.6 | 2.7 | Transit to top | Acquire 2.1 msec |
| 5 | 2.7 | 2.8 | Collect at top surface | |
| 6 | 2.8 | 97.5 | Idle at top surface | |
| 7 | 97.5 | 99.9 | Transit to ITO | |
| 8 | 99.9 | 100.0 | Collect at ITO surface | |
| Repeat from Step 1 | | | | |

Timing.

In order to correctly trigger the time-critical steps in the beginning of the cycle, it is important to know the particle arrival time at the ITO with at least 0.1 msec certainty (i.e., the arrival time window). In one embodiment, bulk particle arrival is detected by a rise in fluorescence using a fast photodiode detector with low-power illumination. In another embodiment, bulk particle arrival is detected by a current drop as particles passivate the electrode surface. In yet another embodiment, bulk particle arrival is detected by a known time interval between switching the field to transport particles from the top electrode to the bottom electrode.

True Force on a Particle.

For the methods of the present invention, a particle force limit of 1 pN was arbitrarily set. This requires knowing the real electric force on the particle during operation of the field-switch cycle. While the computer model described above estimates force as a function of electric field strength, some required user inputs may not be known accurately. For example, the true particle charge is difficult to quantify because of uncertainty in the number of particle-associated counter ions, and the true electric field strength is difficult to quantify due to the steep voltage drop within the electrical double-layers at the electrodes Fortunately, determination of particle transit times allows calculation of particle terminal velocity (i.e., transit distance/transit time), which yields the electric force as follows: at terminal velocity (attained in nanoseconds), the electric force $F_e$ is countered by a drag force $F_d$ (i.e. $F_e + F_d = 0$), wherein $F_d$ is computed from the measured velocity v and the calculated frictional coefficient f (i.e., $F_d = f \times v$, where $f = 6\pi\eta R$, $\eta$=fluid viscosity, and R=particle radius). Since velocity measurements are available at least once per cycle, the true particle forces can be continually monitored.

Particle Stoichiometry.

In yet another embodiment, a particle monolayer in the 100 µm field of view would contain about 7 million DNA particles, each comprising 18 hairpin units of 70 bp each. A total of about 4 million bases could be sequenced, distributed among 200 templates that are each 20 kilobases in length (i.e. 200×20,000=4,000,000). Therefore, the probability that an individual particle will be captured by polymerase and imaged is only about 4/7. Since each particle would carry nearly 300 linked NTPs, there is clearly a plentiful supply of nucleotides for sequencing.

VI. Field-Switch Chamber

In another aspect, the present invention provides a sequencing chamber. The sequencing chamber has a bottom and a top. In one aspect, the sequencing chamber has a first electrode such as on one side of the chamber (e.g., the bottom) of the chamber and a second electrode such as on another side (e.g., the top) of the chamber. A spacer separates the first electrode and second electrode. The spacer can be a polymer, an insulator, a dielectric, a semiconductor or a combination thereof. In yet another aspect, the chamber includes at least one more electrode (e.g., reference electrode, such as Ag/AgCl). The electrodes can be any geometry, such as a ring, a circle, a square, a triangle, and the like.

Figure 7:
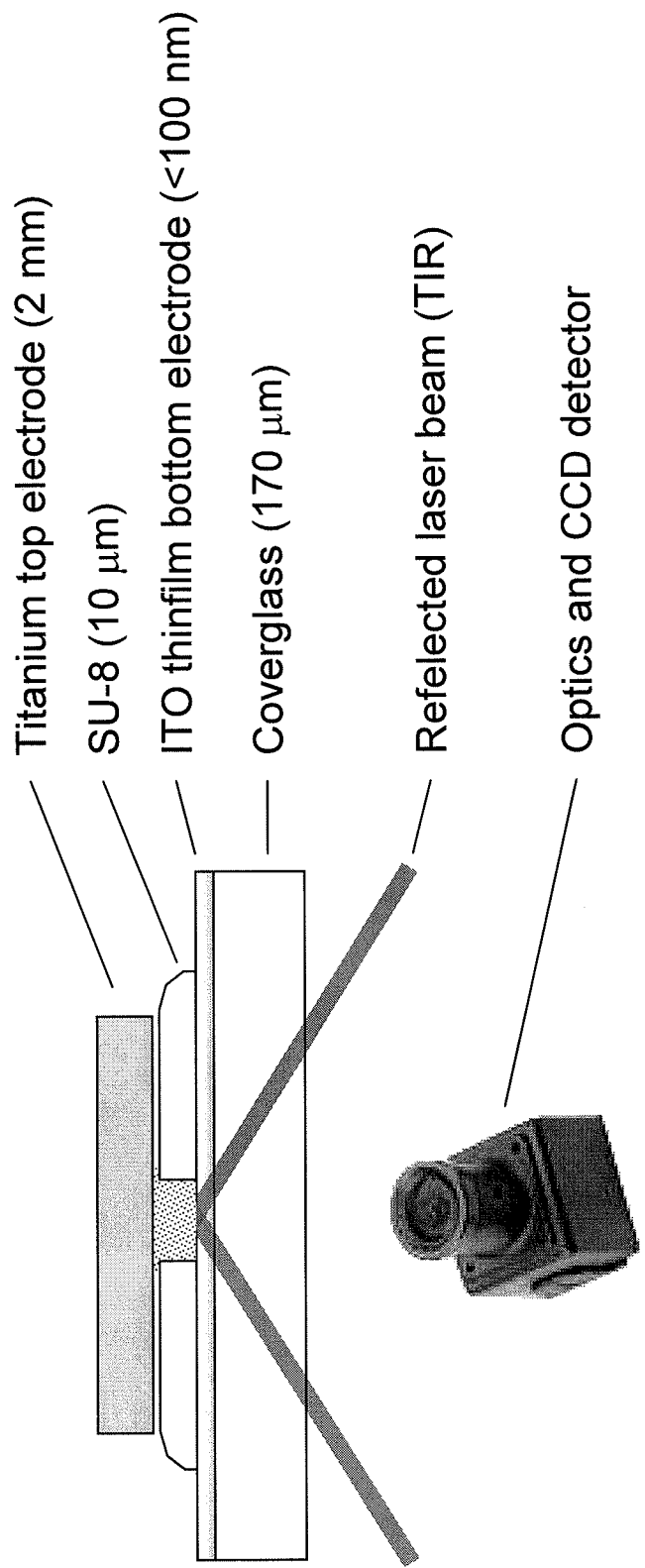
FIG. 7 shows a two-electrode sequencing chamber of the present invention. The bottom and top electrodes are separated by an epoxy (SU-8) spacer film 10 microns thick, as indicated.

As shown in FIG. 7, in one embodiment, the sequencing chamber comprises two working surfaces (e.g., a bottom electrode to which polymerases are immobilized and a top electrode) where particles accumulate as they transit back and forth during the field-switch cycle. The two electrode surfaces are separated by about 5 to 10 microns. In certain aspects, the field-switch cycle operates within the constraints of polymerase kinetics, with the duration of the catalytic step being from about 1-100 msec. Suitable working surfaces for the top electrode include, without limitation, a titanium surface coated with a non-stick permeation layer.

In certain aspects, the first electrode and the second electrode independently comprise any conductor such as a metal, a metal silicide, carbon or a metal oxide. Suitable metals include, but are not limited to, indium, tin, indium-tin, silver, platinum, palladium, titanium, aluminum and gold. Suitable metal oxides include, but are not limited to, indium oxide, tin oxide, indium-tin oxide (ITO), titanium oxide, silver oxide, and aluminum oxide. In certain preferred aspects, the spacer comprises PDMS, SU-8, PET or a combination thereof. In certain other aspects, the first electrode is ITO and is coated with a permeation layer. The second electrode may also have a permeation layer. The permeation layer can be fabricated by controlled polymerization, electropolymerization adsorption, deposition (e.g., from plasma) or by self assembly.

In one embodiment, an electrode permeation layer protects the polymerase, DNA, and particles from electrochemical reactions at the electrode surface, while allowing access to ions and water. In another embodiment, the permeation layer is used to avoid for example, the ~5 nm electrical double layer at the electrode surface, where most of the potential drop occurs between electrodes (Bard et al., In "Electrochemical Methods: Fundamentals and Applications," Wiley & Sons (2001)). Beyond the double layer, the electric field is essentially constant and particles will experience an essentially constant force. The present invention uses a thinner 5-10 nm layer in order to position the polymerases in the evanescent illumination zone. Permeation layers can be formed on ITO by self-assembled monolayers of undecanoic acid (Liron et al., *Biosens. Bioelectron.*, 17:489 (2002)). Alternatively, organic polymers can be deposited in thin (<8 nm) layers by electropolymerization; the polymer itself is nonconducting, but ion-permeable, and it provides a support for covalent protein attachment (Curulli et al., *Electroanalysis,* 13:236 (2001)). Other alternative surface coatings include electropolymerization of biotin-pyrroles, adsorption of $(DOPA)_3$-mPEG, anodization with diols, and crown ether plasmas (respectively: Cosnier et al., Anal. Chem. 71:3692 (1999), Dalsin et al., Langmuir 21:640 (2005), Guo et al., Chem. Pharm. bull 44:860 (1996), Denes et al., J Appl Polymer Sci 81:3425 (2001)). These surfaces can be further passivated with polymers or proteins or other polymers such as polyethylene oxide (PEG), bovine serum albumin, streptavidin, avidin or neutravidin to reduce non-specific adsorption. In one embodiment, streptavidin and related proteins also provide for specific oriented attachment of biotinylated proteins and polymerases. The permeation layer can also be made from a material such as a lipid, which simulates a membrane bound protein.

In one embodiment, the surface is a metal-oxide film such as indium-tin oxide (ITO) or platinum-silicide. In another embodiment, the surface is a metal film such as gold, silver or palladium. In yet another embodiment, the electrode(s) is coated by a permeation layer to isolate immobilized complexes both from electrochemical reactions and from the electrical double-layer occurring at the electrode surface. In other embodiments, the permeation layer thickness is chosen to minimize fluorescence quenching by metals in the electrode while maintaining the complexes in the evanescent wave associated with total internal reflection microscopy. In still other embodiments, the angle of incidence of the excitation light is chosen to allow for surface plasmon excitation at the electrode surface. In certain instances, the plurality of complexes are immobilized onto the surface by covalent bonding. In certain other instances, the plurality of complexes are immobilized onto the surface by ionic bonding. In still other instances, the plurality of complexes are immobilized onto the surface by macromolecular bonds such as avidin-biotin or antibody-epitope interactions.

In another embodiment, the top electrode is, for example, a titanium or gold disk covered with a non-stick permeation layer as described for the bottom electrode (above).

VII. Examples

The following examples are offered to illustrate, but not to limit, the claimed invention.

Example 1

Field-Switch Chamber Construction

This example illustrates the construction of a 10 µm×250 µm two-electrode sequencing chamber of the present invention comprising a spin-coated SU-8 spacer permanently bonded to an ITO-coated coverslip. The ITO surface in the bottom of the chamber is then coated with a permeation layer by controlled electropolymerization with biotin-pyrrole. The chamber is closed with a top electrode.

Chamber Construction.

Microscope coverslips (25×25×0.17 mm) are coated with ITO to a resistivity of 140 ohm/square and refractive index 1.52 (ZC&R Inc.). The coverslips are cleaned by successive washes in Decon 77, deionized water and chloroform. After oven-drying for 30 min and cooling to room temperature, the coverslips are coated with 10 um of SU-8 photoresist by spin casting. The resist is exposed with collimated UV light through a contact mask to give a 250 um diameter hole and a 2×2 mm contact pad. The photoresist is then baked and developed (Shipley Microposit EC solvent).

ITO Permeation Layer.

The ITO surface in the bottom of the 250 µm×10 µm PDMS well is next coated with a permeation layer by electropolymerization with biotin-pyrrole as described in Kuramitz et al., Electroanalysis 15:225 (2003). The polymer surface is then coated with Neutravidin (Konry et al., Anal Chem 75:2633 (2003)).

Top Electrode.

A titanium disk (3 mm diameter×2 mm thick) coated with mPEG-DOPA$_3$ (Dalsin et al., Langmuir 21:640 (2005)) is used as the top electrode. After a sample is applied to the chamber, excess fluid is squeezed out as the top electrode is set in place and the chamber is sealed by a drop of mineral oil. Electrical contact is made to the top exposed surface of the electrode disk.

Example 2

Construction of a DNA Nanoparticle by Rolling Circle Replication

Template Construction.

Figure 8:
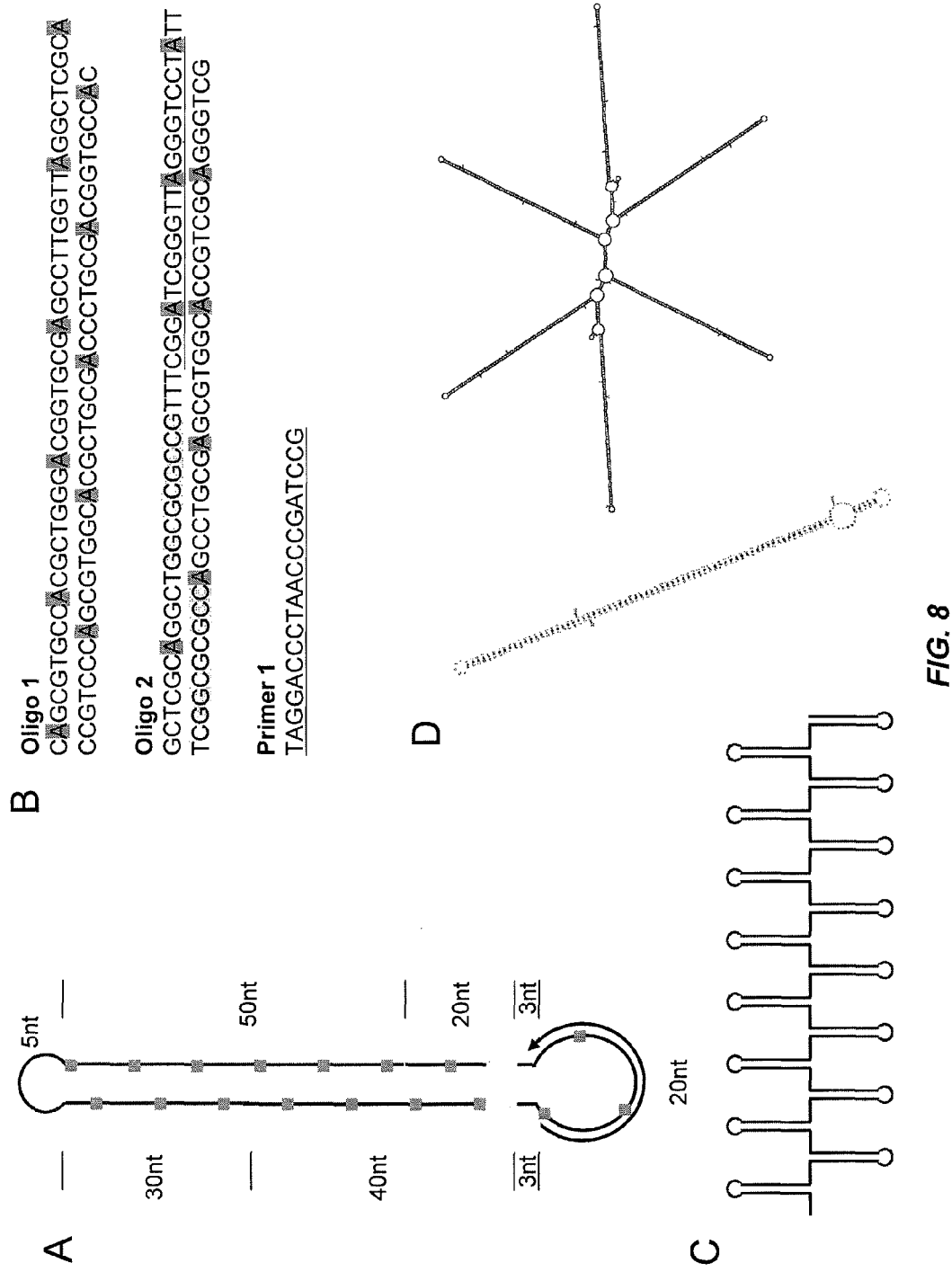
FIG. 8 A-D Panel A shows a "dumbell" template for production of hairpin particles by rolling circle replication. The 20 nucleotide loop (bottom) is complementary to the primer (circle with arrow). Adenosine bases in the template (squares) allow incorporation of thymidine or uracil bases in the product strand; substituting amino-modified dUTP for dTTP provides amine functionality for attachment of SYBR-dNTP moieties. Panel B shows example oligonucleotides for template construction; oligos 1 and 2 (SEQ ID NOS:2 and 3) are ligated into the dumbell, and primer 1 (SEQ ID NO:4) is used for rolling circle replication by polymerases capable of strand-displacement polymerization. Panel C shows the rolling circle product, comprising tandem hairpins. Panel D shows secondary, structures predicted by mFold software for a single hairpin unit (SEQ ID NO:5) and for a 6-hairpin particle.
Figure 9:
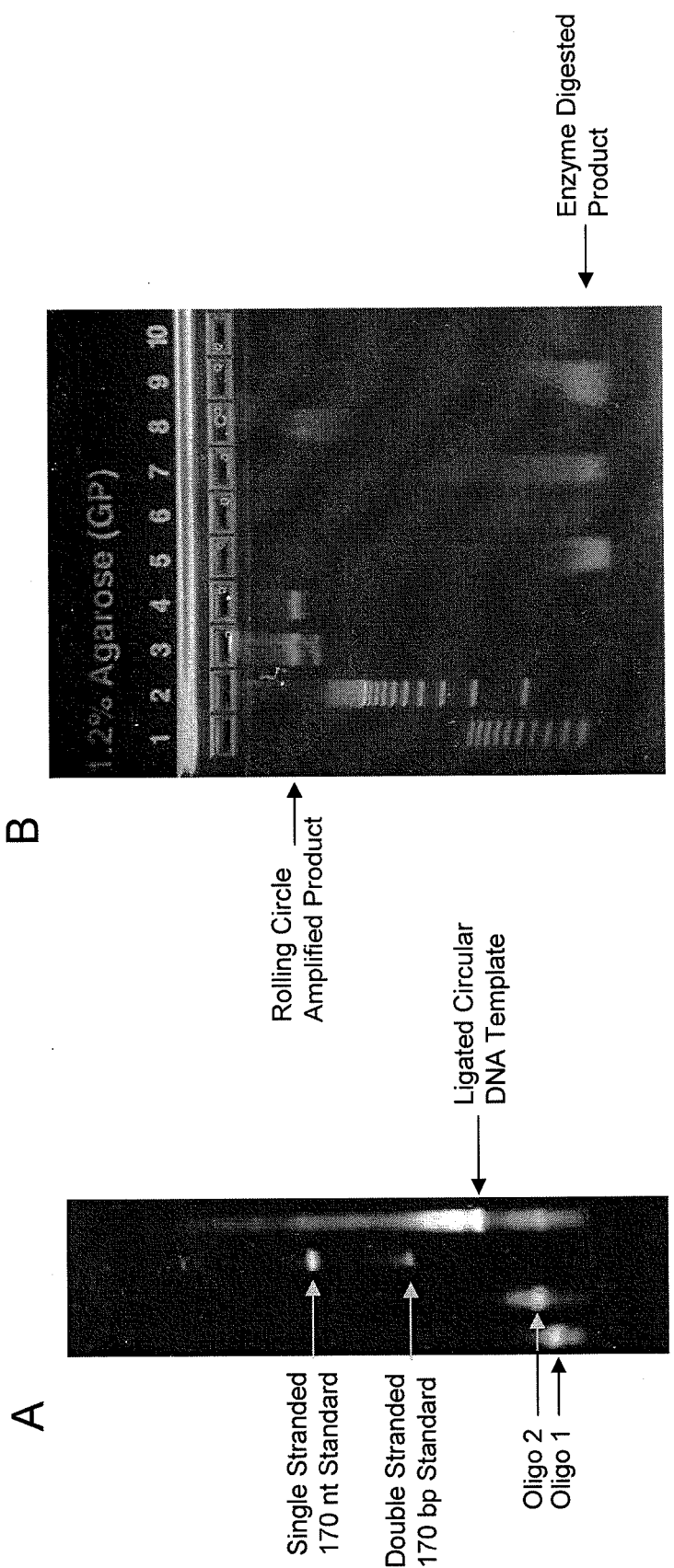
FIG. 9 A-B Panel A shows ligation of oligos 1 and 2; the resulting "dumbell" template is purified for use in rolling circle replication by excising the indicated band from the gel. Panel B shows the rolling circle replicated products made with dTTP (lane 3) or aha-dUTP (lane 4; Molecular Probes). Lanes 1-2 are size markers. Lanes 5-9 are enzyme digested particles, showing reduction to 6-hairpin units.

The circular template used for the rolling circle amplification was constructed by ligating two 5' phosphate-labeled oligos (oligo 1 and oligo 2) that contain regions of inverted repeated DNA, forming a hairpin structure (FIG. 8 a-b). Ten pmoles of each oligo were combined with 1× final concentration of T4 ligation buffer (New England Biolabs) in a volume of 20 uL. The mixture was incubated at 90° C. for 1 min and then cooled to 20° C. T4 DNA ligase (100 units, New England Biolabs) was then added to the reaction mixture and incubated at 24° C. for 3 hours. The ligated template was purified on a 6% TBE-Urea denaturing acrylamide gel, cutting the ligated circular template from the gel, and extracting the DNA from the gel fragment by incubating in 10 mM Tris pH 8 for 8 hours at 20° C. (FIG. 9a).

In one embodiment, a DNA particle is constructed by rolling circle amplification of a DNA template (FIG. 8a). This produces a DNA particle comprising multiple identical hairpin units linked along a single strand. In one embodiment, the template for the rolling circle amplification may is a primed single stranded circular DNA strand that contains a region where a specific DNA oligo primer will hybridize to the template and initiate rolling circle amplification. In another embodiment, the template is partially self-complementary, forming a "dumbell" structure with a primer binding region on one of the single-stranded loops. In yet another embodiment, the template sequence is constructed in such a way to allow incorporation of a modified nucleotides, such as 5-aminohexylacrylamido-dUTP (Aha-dUTP) (Molecular Probes), at specific positions along the amplified product (FIG. 8a-b). Rolling circle amplification can be accomplished either with DNA or RNA polymerases having strand displacement activity. In one embodiment, the template may be designed to provide restriction enzyme recognition sites in order to trim the amplified product to a desired size range, giving particles comprising one or more units. In another embodiment, the particle size can be controlled in the rolling circle amplification reaction by limiting the reaction time or limiting the amount of dNTPs.

Rolling Circle Amplification.

A mixture of 30 fmoles of template DNA, 500 fmoles of an oligo primer, 1 mM final concentration of each natural or modified dNTP, 1× final concentration of phi29 reaction buffer (New England Biolabs), 100 µg/ml BSA, and 5 units of phi29 DNA polymerase were incubated in a 25 uL volume for 3 hours at 30° C. The amplified product consists of repeating units of DNA hairpins (FIG. 8c) (FIG. 9b). mFold computer analysis, estimating the most stable confirmation for the DNA structures, for a single hairpin unit and for a series of six hairpin units is shown (FIG. 8d).

Enzymatic Cleavage of Rolling Circle Amplified Products.

Rolling circle products made with dATP, dCTP, dGTP, and either dTTP (FIG. 10b lanes 3, 5, 7, and 9) or Aha-dUTP (FIG. 9b lanes 4, 6, 8, and 10) were produced. The products were digested with restriction enzymes BstUI (recognition site CGCG) BstUI (FIG. 9b lanes 5 and 6), BssHII (recognition site GCGCGC) (FIG. 9b lanes 7 and 8), or AscI (recognition site GGCGCGCC) (FIG. 9b lanes 9 and 10). Lanes 1 and 2 contain 50 bp and 500 bp DNA standard ladders.

Example 3

Synthesis of dCTP-PEG8-Cys-SYBR-101

Figure 10:
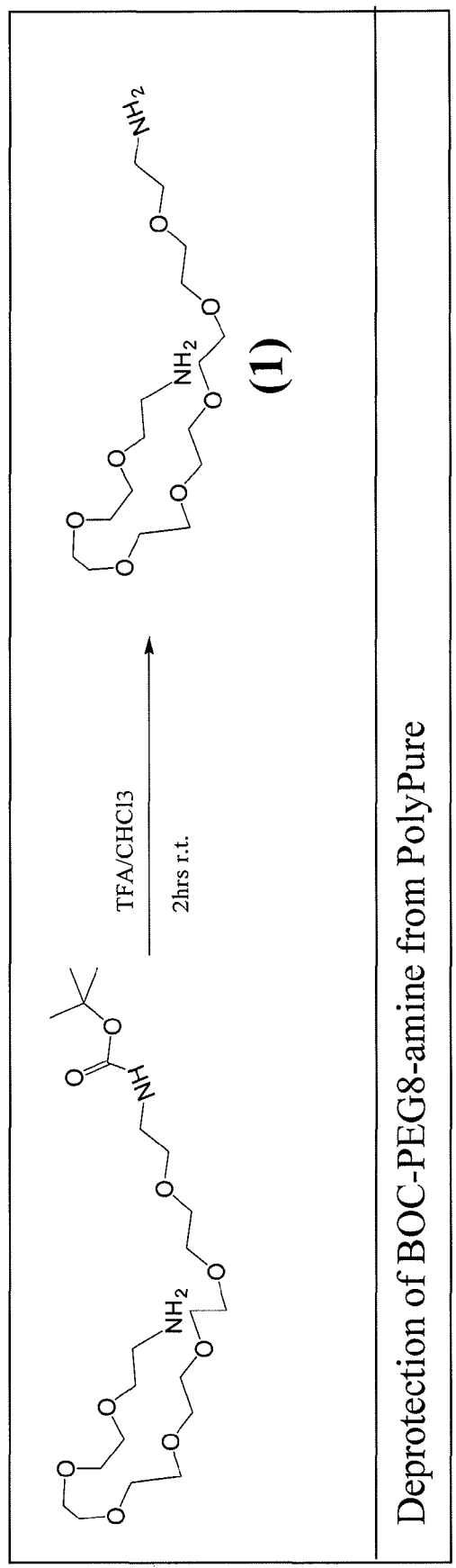
FIG. 10 shows deprotection of BOC-PEG8-amine (Polypure), performed before coupling to a nucleotide.

Deprotection of BOC-Amino PEG Amine (FIG. 10, cpd 1).

Figure 11:
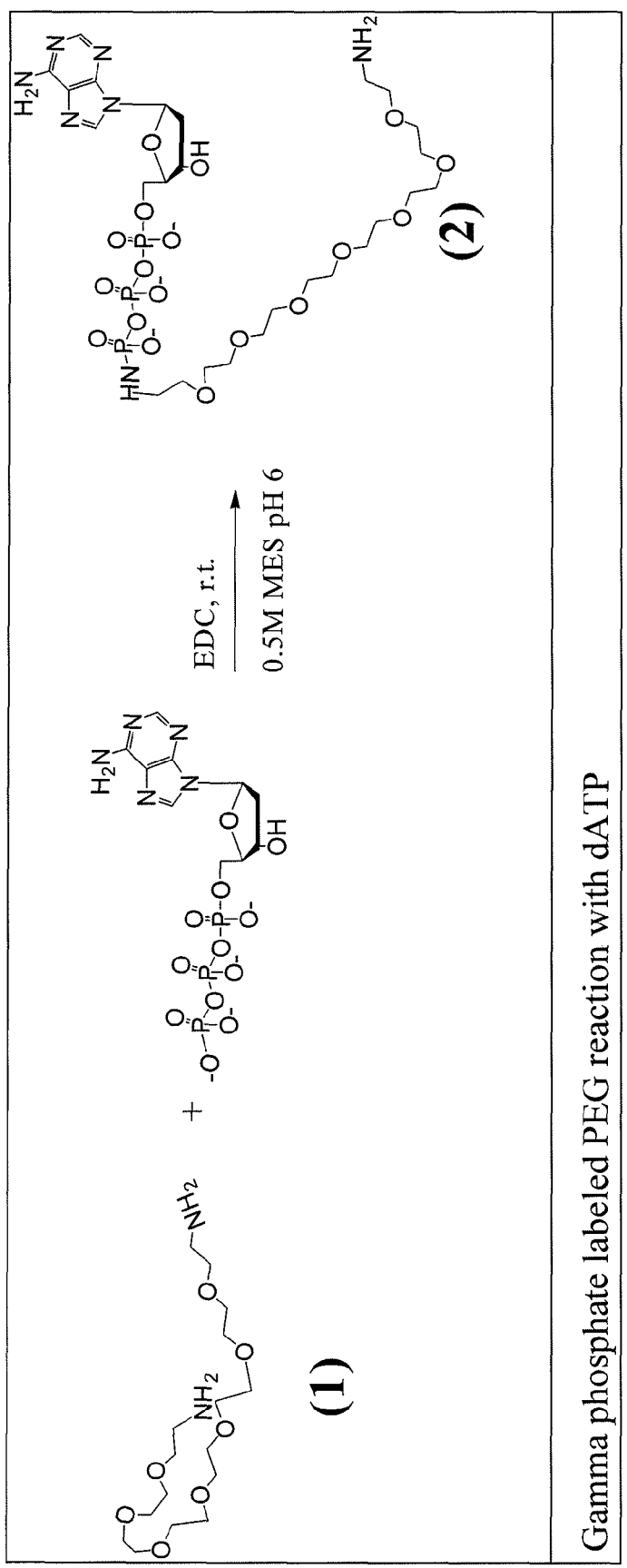
FIG. 11 shows coupling of the deprotected PEG8 diamine (from FIG. 10) to the terminal phosphate group of dATP.

BOC-amino PEG amine (PolyPure, 1 gram), was added to a trifluoroacetic acid/chloroform solution (1:1 v/v, 20 mL). Reaction was stirred at room temperature for 2 hours. NaHCO$_3$ (10 mL, 10 mM) was slowly added to the reaction. The aqueous layer was separated from the organic layer and retained. Chloroform was added and two extractions (20 mL each) were performed. To the aqueous layer, ethyl ether (20 mL) was added and the extraction was performed twice. The aqueous layer was dried in vacu. The final product was a clear oily residue, and weighed approximately 1 gram. Yield was estimated at less than 100% due to possible salts and water still present in sample. $^1$H NMR, D$_2$O: delta 3.675 (t, 4H), 3.61 (m, 24H), 3.1 (t, 4H). ESI MS [M+1] calculated 369.3. observed [M+1] 369.2.

dATP-PEGS-Amine (FIG. 11, cpd 2).

13.3 mg dATP from Sigma (24.8 µmol, 1 equiv) and 190.6 mg EDC from Aldrich (992 µmol, 40 equiv) were added together in 500 mM MES buffer pH 5.8, giving final concentrations 79 mM and 3.2M, respectively. The reaction proceeded at room temperature for 10 minutes. A PEG-diamine (1) solution (750 mM, 186 µmol, 7.5 equiv) in 500 mM K-MES buffer pH 6.0 was added to the dATP/EDC (248 uL). The reaction proceeded at room temperature overnight. The large excess of reagents and overnight reaction converted the entire amount of starting material to desired product. The product was first purified on a HiPrep™ DEAF 20 mL column from Amersham with buffers A and B (A: 10 mM phosphate+20% ACN and buffer B: Buffer A in 1M NaCl). LC conditions: 0-10 min 0% B, 10-15 min 0-100% B, 15-20 min 100% B at a flow rate of 10 mL/min. The free PEG eluted from the column in void volume. The nucleotide conjugate product eluted as a broad peak at 5-10 minutes. This broad peak was collected and dried in vacu. The product was further purified on a 30×250 mm 10 um Inertsil ODS-3 column from Varian, with buffer system A and B (A: 100 mM TEAAc (pH 6.6) with 4% ACN and B: 100 mM TEAAc (pH 6.6) with 80% acetonitrile). LC conditions: 0-5 min 0-15% B, 5-10 min 15-20% B, 10-20 min 20-100% B with a flow rate of 20 mL/min. The product eluting at 12 minutes was collected and dried in vacu. Yield averaged 30% after purification steps. $^1$H NMR D$_2$O: delta 8.52 (s, 1H), 8.27 (s, 1H), 6.5 (t, 1H), 4.3 (t, 1H), 4.2 (m, 1H), 4.1 (m, 1H), 3.8 (m, 2911 overlaid with contaminant), 3.2 (t, 2H+contaminant), 3.1 (m, 2H+contaminant), 2.8 (m, 1H), 2.6 (m, 1H). Contaminants present in sample were TEAAc and glycerol. ESI-MS [M+1] calculated 842.25, observed [M+1] 842.3.

Figure 12:
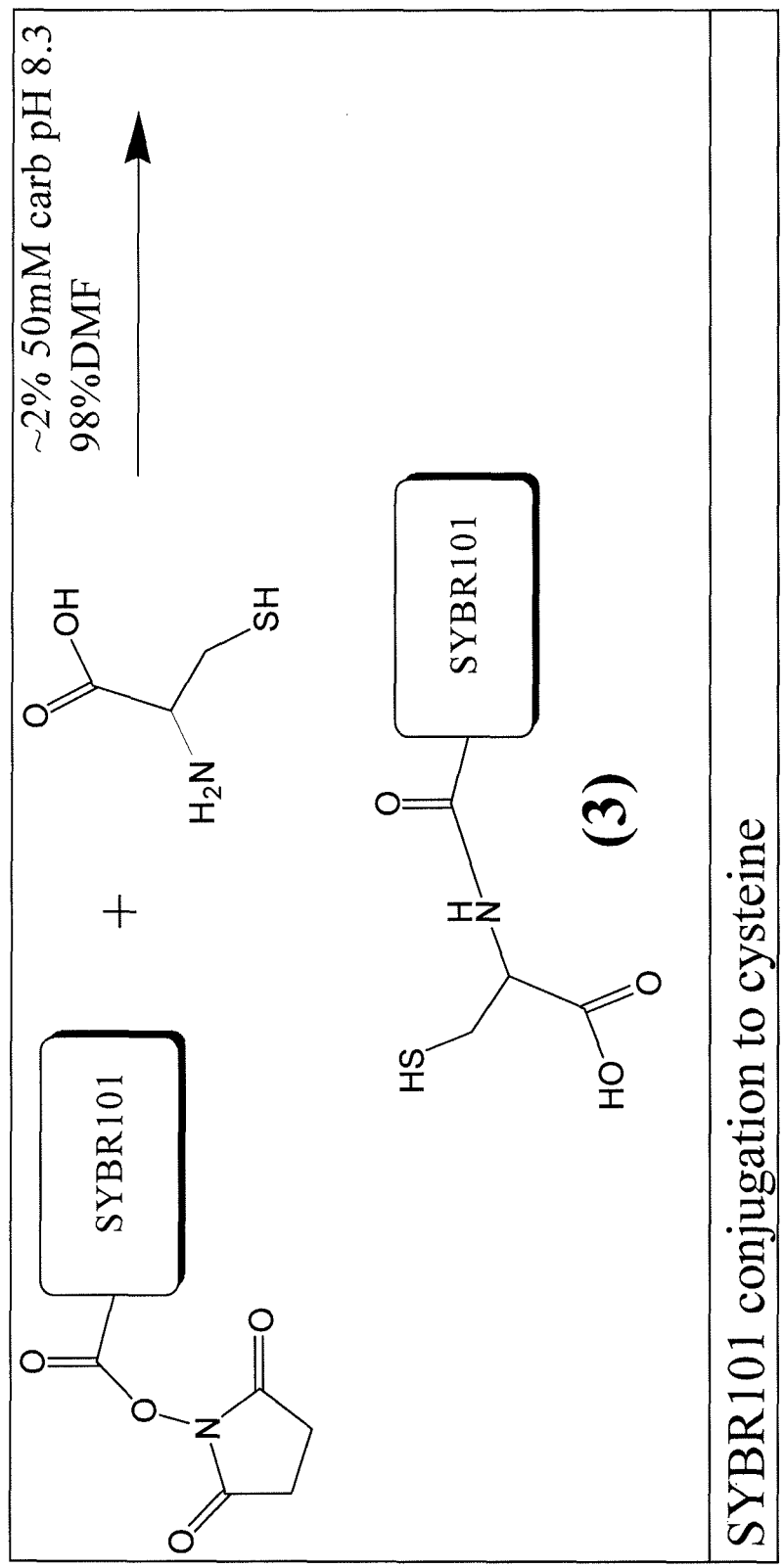
FIG. 12 shows coupling of SYBR-101 NHS (Molecular Probes) to cysteine.

SYBR101-Cysteine (FIG. 12, cpd 3).

Figure 13:
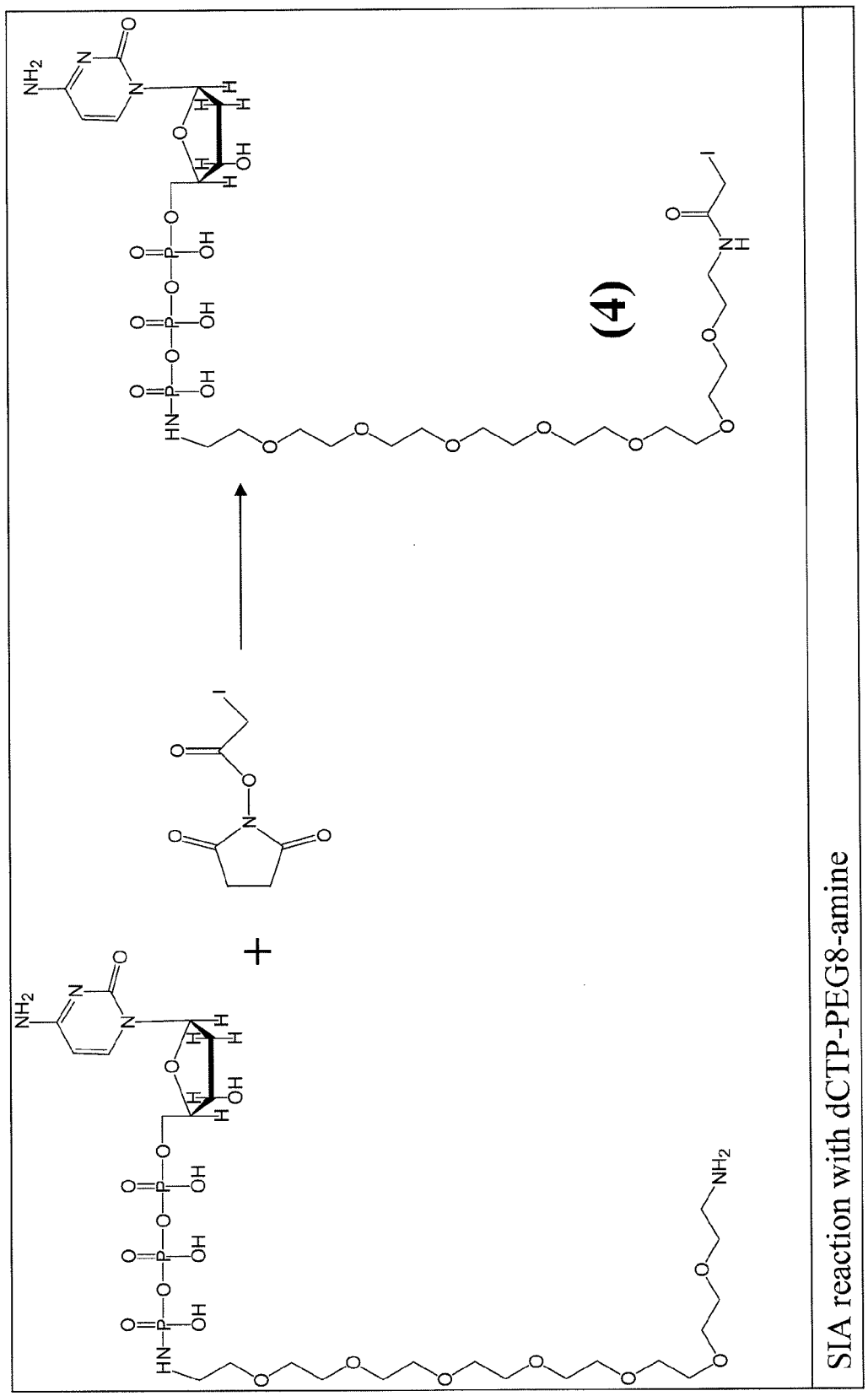
FIG. 13 shows activation of dCTP-PEG8-amine with SIA. This converts the amine to iodoacetamide functionality for subsequent reaction with a thiol.

SYBR101-NHSE purchased from Molecular Probes (1 mg/mL in DMF, 1.7 mM, 400 uL, $6.8e^{-4}$ mmol) was added to a cysteine solution dissolved at 50 mM with carbonate buffer pH adjusted to 8.3 (Sigma, 100 mM, 6.8 uL, $6.8e^{-4}$ mmol). The two compounds were added together and allowed to react at room temperature, protected from light, for 30 minutes. ESI-MS[M+1] calculated 585.2. observed [M+1] 585.2. The product was not purified. Estimated product yield: 80%.

dCTP-PEG-IA (FIG. 13, cpd 4).

Figure 14:
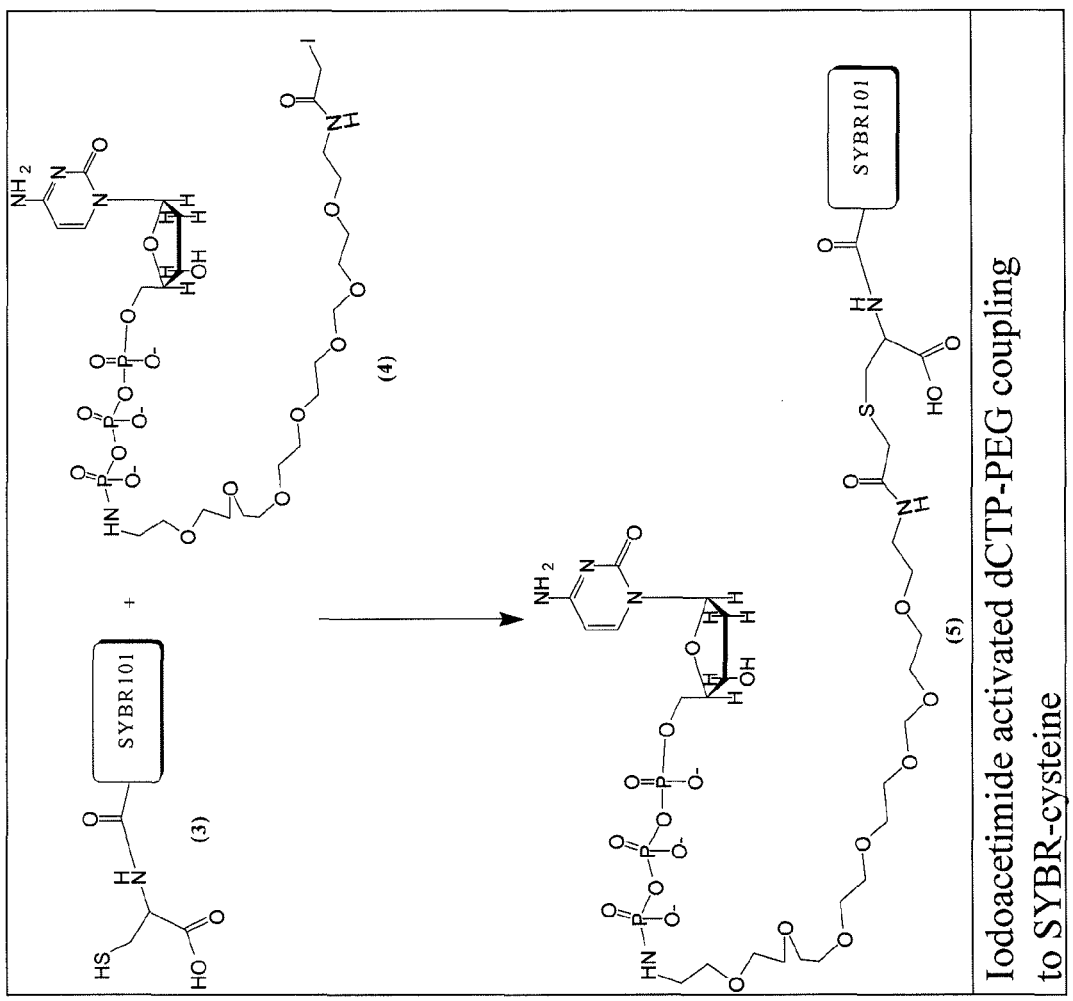
FIG. 14 shows the synthesis of SYBR-dCTP with carboxylate functionality contributed by the connector moiety (cysteine).

This reaction should be run at the same time as the previous reaction. dCTP-PEGS-amine (FIG. 11, cpd 2; dCTP starting nucleotide instead of dATP) was reconstituted in DMSO (20 mM, 34 uL, $6.8e^{-4}$ mmol). SIA purchased from Pierce was dissolved in DMSO (10 mM, 68 uL, $6.8e^{-4}$ mmol,). The final concentration of nucleotide in the reaction was adjusted to 5 mM with 34 uL buffer (100 mM sodium phosphate, 0.15M NaCl, pH 7.4). Reaction proceeded at room temperature, protected from light, for 30 min. Reaction, monitored by C18 HPLC, was finished after 30 min. The dCTP-PEG-IA product was not purified. Estimated product yield: 75%.

dCTP-PEG8-cys-SYBR101 (FIG. 14, cpd 5).

Entire reactions of unpurified (3) and (4) were added together. Reaction proceeded at room temperature for 18 hours, protected from light. Reaction was then purified by HPLC. LC conditions were 20-100% B over a period of 15 min (buffer A was 100 mM TEAAc (pH 6.6) with 4% ACN and buffer B was 100 mM TEAAc (pH 6.6) with 80% acetonitrile at a flow rate of 3 mL/min. LC column was a Polaris 3 um, 10×150 mm (Varian). Product eluted at 8 minutes and was dried in vacu. LC ESI-MS[M+1] calculated 1442.4. Observed [M+1] 1442.4. Estimated product yield: 80%.

Example 4

Illustrates the Use of Applied Force

Nanoparticle transport out of the evanescent detection zone is fast (i.e., <0.5 msec) so that bound particles can be imaged prior to completion of the base addition reaction (i.e., 1-100 msec). Particle transport can be arbitrarily fast if enough force is used. Two force constraints related to (1) stretching of the DNA template and to (2) the strength of nucleotide binding to the polymerase have been identified.

The first force constraint comes from observations that physical stretching of a DNA template influences the activity of RNA and DNA polymerases (Wuite et al., *Nature*, 404:103 (2000); Forde et al., *PNAS*, 99:11682 (2002); Goel et al., *PNAS*, 98:8485 (2001)). For T7 DNA polymerase, as the DNA stretching force increases from 0 to 35 pN, polymerase activity initially increases slightly as the force ramps up to ~5 pN, but then decreases back to the initial rate at ~10 pN, and finally is inhibited completely at a stretching force 35 pN. The slight activity increase at low force may relate to the straightening of random-coil DNA, making it a better substrate for the enzyme, whereas the inhibition at a higher force may be caused by a change in helical pitch and DNA denaturation (Rouzina et al., *Biophys. J.*, 80:882 (2001)). As such, an upper stretch force limit of 10 pN was set based on the observation that forces above this level inhibit polymerase activity. For a 20 kb DNA template (q=−40,000), the 10 pN limit would occur at a relatively low field strength (i.e., E=1600 V/m (f=q×E; see also below)).

The second force constraint is related to the physical strength of the bond between a nucleotide triphosphate and a polymerase. The electric force on the nucleotide must not be so great as to pull the nucleotide from the polymerase before the catalytic reaction is completed. For example, T7 DNA polymerase in a closed conformation displays a strong interaction with a nucleotide, whereby the ribose and triphosphate moieties of the nucleotide are contacted extensively by conserved residues and by two metals that coordinate the unesterified oxygens of all three phosphates (Doublie et al., *Nature*, 391:251 (1998)). Such interactions also apply to most other DNA polymerases (Patel et al., *Nat. Struct. Biol.*, 8:656 (2001)). The catalytic reaction occurs in the closed conformation, in which the nucleotide is tightly bound. After nucleotide incorporation, the polymerase changes to an open conformation from which pyrophosphate is released.

To estimate the force limit in the systems of the present invention, a simple and conservative approach was taken to first estimate the thermal force scale likely to produce rapid, exponential increases in nucleotide dissociation rate and then limit the applied force to lower values. This approach ensures that the applied electrical force is weak compared to the level of force needed to rapidly dissociate the nucleotide and the nucleotide will remain bound under force up to its natural time for spontaneous dissociation. To make the calculation, a thermal force scale $f_\beta$ can determined from the ratio of thermal energy $k_BT$ (Newton-meter) to the distance $x_\beta$ (meter) expected to be gained along the force direction in nucleotide dissociation according to the formula: $f_\beta=k_BT/X_\beta$. Of particular relevance here, the length scale $x_\beta$ has been measured for the weak interaction between a protein, L-selectin, and its polysaccharide ligand, $sLe^x$ (Evans et al., *PNAS*, 98:3784 (2001)). Two length scales were found for both a strong interaction with a length $x_\beta$=0.6-1.0 Å (likely due to coordination of $sLe^x$ by one $Ca^{++}$ atom) and a weak interaction with length $x_\beta$=4 Å (likely due to electrostatic and hydrogen bonds).

The L-selectin example is similar to polymerase-nucleotide binding in the sense that both involve metal ion coordination and both have a like multiplicity of weaker electrostatic and hydrogen bonds. This comparison suggests that the nucleotide, coordinated by two $Mg^{++}$, is likely to be bound as tightly as the fucose ring of the polysaccharide, which is coordinated by one $Ca^{++}$. Although the small length scale for metal ion coordination implies a very large thermal force scale, conservative estimations can be made such that the bond rupture distance is governed by the weaker hydrogen bonds, $x_\beta$~3-5 Å. Since $k_BT$=4.1 pN-nm at room temperature, this conservative estimate leads to a much smaller value of thermal force scale, $f_\beta=k_BT/x_\beta$=8-13 pN. For the systems of the present invention, an upper limit of 1 pN on the particle, less than 12% of thermal force, was arbitrarily set. A 1 pN force should have negligible effect on a bound nucleotide. The required electric field strength depends on particle charge, which in turn depends on particle structure.

Example 5

Illustrates a Computer Model of the System

Figure 15:
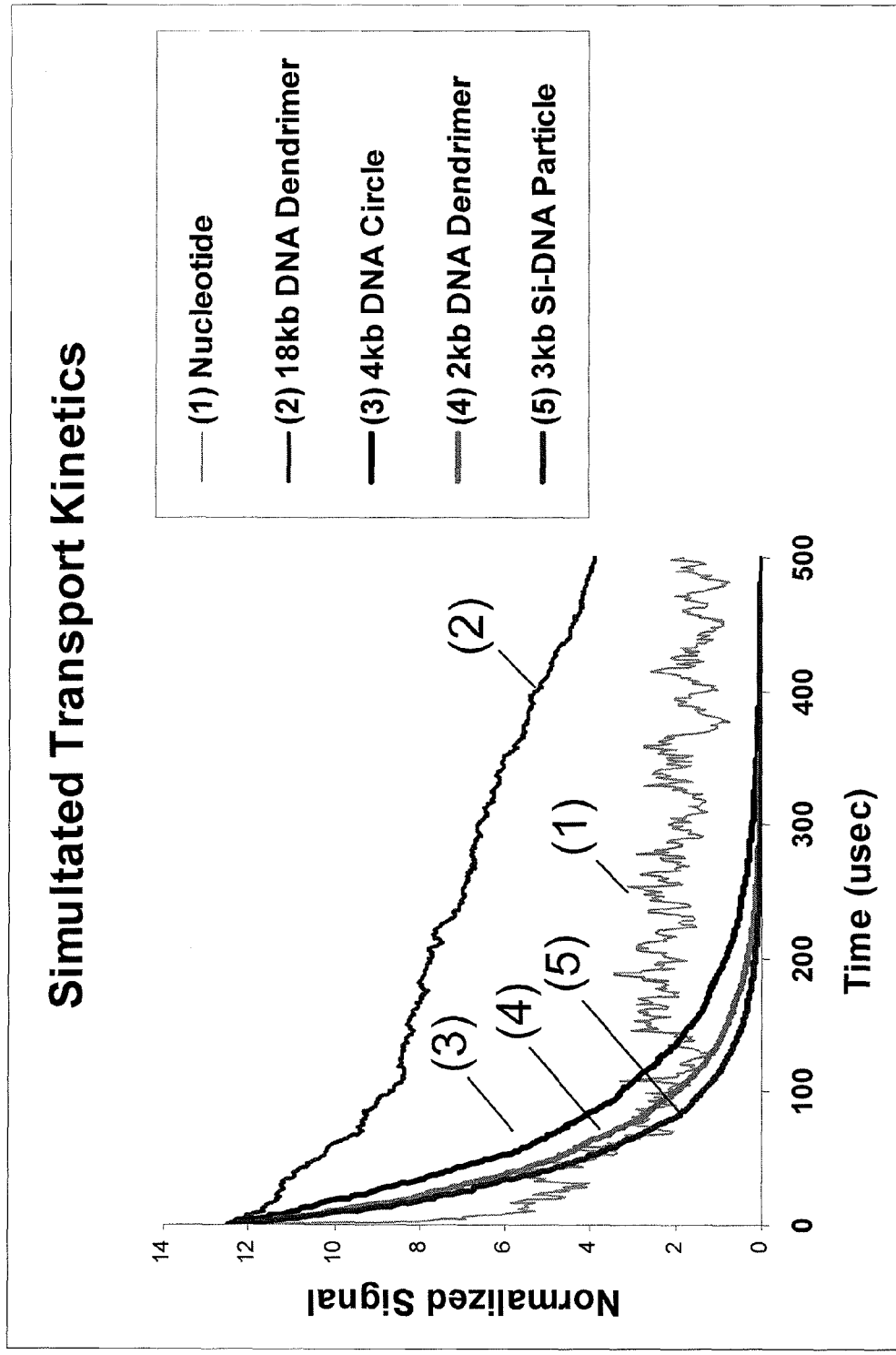
FIG. 15 shows the electrokinetic properties of 5 simulated particle types: a labeled dNTP not attached to a nanoparticle (curve 1); a DNA dendrimer (curve 2); a 4 kb circular DNA (curve 3); a 2 kb circular DNA (curve 4); and a 55 nm silica- DNA particle having about 50 each of 120-base Y-branched oligonucleotides attached to ~20 nm diameter silica particles (curve 5).

A computer model was developed to simulate individual particles under electric and thermal forces (random-walk diffusion) while tracking the fluorescence signal over time. In an evaluation of nearly 7,000 combinations of different values of the 8 input parameters, the best performing particles were small and highly charged, allowing them to experience enough force (f=q×E) for fast transport, given the two force constraints described above. The electrokinetic properties of 5 example particles are shown in FIG. 15 and Table III. In each case, the E-field was the highest possible, limited either by force on the particle (1 pN) or force on the template (10 pN). The total fluorescence signal ($S_T$) detected at one pixel of a CCD camera is the sum of contributions ($s_i$) from all particles in that pixel ($S_T = \Sigma s_i$). The signal is scaled so that $s_i=1$ for an individual particle excited by the maximum evanescent energy at the electrode surface.

TABLE III

Particle Transport Kinetic Parameters.

| Parameter | dNTP-Dye | Dendrimer | DNA Circ | DNA Circ | SiDNA Part |
|---|---|---|---|---|---|
| Bases | 1 base | 18 kb | 4 kb | 2 kb | 3 kb |
| Dia, nm | 3 | 180 | 300 | 200 | 55 |
| Charge q | −5 | −36000 | −7200 | −3600 | −5400 |
| Diff m2/s | 1.5E−09 | 4.8E−12 | 1E−11 | 1.6E−11 | 1.6E−11 |
| Fric kg/s | 3.1E−12 | 9.4E−10 | 4.5E−10 | 2.9E−10 | 2.8E−10 |
| E-field V/m | 1560 | 168 | 867 | 1560 | 1160 |
| F (particle) pN | 0.0012 | 1 | 1 | 0.9 | 1 |
| F (DNA) pN | 10 | 1.1 | 5.56 | 10 | 7.7 |
| Veloc nm/usec | 0.4 | 0.47 | 2.2 | 3.1 | 3.5 |
| td usec | >1000 | >1000 | 360 | 260 | 218 |
| Dye Content | 1 | 400 | 400 | 200 | 300 |
| Illum Index | 1 | 0.67 | 0.25 | 0.44 | 0.85 |
| Dye Equiv | 1 | 268 | 100 | 88 | 255 |

In FIG. 15, $S_T$ was monitored for 1 msec as a monolayer of particles moved outward from the surface. The initial signal STO=13 for a monolayer of 55 nm particles. This is because roughly 13 particles comprise a monolayer over a 200×200 nm pixel area (($200)^2/(55)^2=13$). In order to compare signals across all 5 particle types, 13 particles were modeled arbitrarily for the other 4 types, regardless of their diameter. A time $t_d$ is defined when $S_T$ falls below a threshold $S_T<0.1$; that is, after time $t_d$, an individual bound particle $s_i=1$ can be detected with little background from unbound particles. FIG. 15 shows good results with low mass DNA structures: $t_d=360$ and 260 μsec for 4 kb and 2 kb circular DNA (curves 3 and 4, respectively); and $t_d=218$ μsec for the 55 nm silica-DNA particle (curve 5). The computer model indicates that fast transport kinetics are possible.

A. Nanoscale Particle Size to Maximize Detectability and Nucleotide Concentration Detectability.

An illumination index was computed for each particle type (see, Table III above) by summing the position-weighted illumination of each dye location and dividing by the total number of dyes in the particle. As shown in Table III, a silica-DNA particle (300 dyes) would be more than twice the brightness of the 4 kb DNA circle (400 dyes), even though the small particle contains fewer dyes. As such, small particles are preferred because they are more fully illuminated.

Nucleotide Concentration.

The field-switch sequencing method of the present invention offers the advantage of actively concentrating particles at the electrode surface, providing a high concentration of dNTPs for the immobilized polymerases during the binding phase of the sequencing cycle. Small particles are preferred because they have a higher diffusivity (i.e., more collisions with immobilized polymerases), a higher surface-to-volume ratio (i.e., more dNTPs attached per unit particle volume), and superior coverage (i.e., many small particles cover the electrode surface better than a few large particles).

$K_m$ values for free nucleotides in solution binding to DNA polymerases are typically <0.1 mM. To help estimate the binding ability of DNA polymerases for nucleotides linked to nanoparticles, the density of nucleotides was calculated on a particle surface (nucleotides/area). The value obtained was then correlated to bulk molar nucleotide concentrations (nucleotides/volume). The calculation involved computing the nucleotide parking area pA (i.e., Å$^2$/nucleotide), wherein pA=(particle surface area)/(nucleotides per particle). If the surface-bound nucleotides are thought of as being in bulk solution, each would occupy a parking volume pV (i.e., Å$^3$/nucleotide), such that pV=pA$^{3/2}$. In this view, 100 surface nucleotides on a 55 nm particle equate to 1.8 mM, which is sufficient to support fast nucleotide binding based on DNA polymerase binding kinetics in free solution (i.e., $K_m<0.1$ mM).

While high nucleotide surface density, flexible tethered nucleotides, and high particle concentrations at the electrode can all have positive effects on polymerase binding kinetics, the lower diffusivity of particles compared to free nucleotides can have a negative effect. However, every polymerase does not have to bind a nucleotide every cycle. Missed binding events can be remedied in subsequent cycles, with the only impact being on system efficiency.

B. Fast Detection in Four Colors

Detection.

In one embodiment, a four color single molecule imaging microscope with total internal reflectance (evanescent wave) excitation and a CCD camera to image a 100 μm×100 μm field of view can be used. The camera is, e.g., a Micromax 512× 512 or a Pentamax intensified CCD from Roper Scientific. However, the Micromax is better with respect to the signal to noise (SN). The mean background noise with the laser on is 10 electrons. With 2×2 pixel binning and a 2 MHz readout, the total frame readout time is 33 msec, which is compatible with a 100 msec field-switch sequencing cycle. Single immobilized TAMRA molecules are typically imaged in 80 msec with an SN of ~11.

Since SN scales linearly with integration time, TAMRA would be undetectable (SN <0.28) in the 1-2 msec timeframe required for field-switch sequencing. Although photodiode point detectors have greater sensitivity than CCD detectors, one objective of the present invention is to increase throughput 200-300 fold over what a point detector could deliver by imaging many single, immobilized polymerase-DNA complexes simultaneously with a camera.

Stability of Intercalated Complex.

The NMR structure of a TOTO-DNA intercalation complex reveals a distorted double helix unwound by 12° and extended in length about 12% (Spielmann et al., *Biochemistry*, 34:8542 (1995)). Nonetheless, dye intercalation stabilizes DNA against denaturation, as shown by a $T_m$ change from 65° C. to 95° C. upon intercalating 6 YOYO dyes into a 30-mer dsDNA oligonucleotide (Bjorndal et al., *Biopolymers*, 65:40 (2002)). This dye family is marketed for staining DNA prior to electrophoresis based on experiments showing that complexes comprising 1 dye:7-10 base pairs remain fluorescent in agarose gels (Rye et al., *Nucleic Acids Res.*, 20:2803 (1992)). These findings have been extended by quantifying the JOJO:DNA ratio of complexes in a dialysis bag in an electric field (1000 V/meter). At different times, the sample was removed from the bag and the dye:DNA ratio was determined spectrophotometrically. The sample was returned to the same bag and the process was repeated for the next time point. Variations in sample recovery at each time point had no effect on the measured dye:DNA ratio. In this experiment, the dye:DNA ratio was stable. In another embodiment, dyes such as SYBR-101, having a functional group for conjugation, would not only intercalate into DNA but would also be covalently linked to amino-modified DNA, are used in the present invention. Covalent linkage can thus prevent any possibility of dissociation of the dye from the DNA under conditions of elevated temperature, salt concentration, detergents or organic solvents that tend to decrease the binding affinity between dye and DNA All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for detecting a catalytic event having improved binding kinetics, said method comprising:
   (a) immobilizing a target nucleic acid, a primer nucleic acid, and a polymerase onto a surface;
   (b) contacting said surface with a plurality of nanoparticles, wherein each nanoparticle comprises a plurality of nucleotide phosphates (NPs), which are substrates for the polymerase, wherein each of said plurality of nucleotide phosphates (NPs) is attached to the nanoparticle via a linker, wherein the nanoparticle size, the linker and the NP density on the nanoparticle surface are selected such that the $K_m$ for the binding of nanoparticle-immobilized NPs to the polymerase is lowered compared to the $K_m$ for a free nucleotide in solution binding to the polymerase; and
   (c) detecting polymerase-mediated incorporation of at least one of said plurality of nucleotide phosphates into a single molecule of the primer nucleic acid to detect said catalytic event, wherein the nanoparticle is released from the nucleotide phosphate upon incorporation, and wherein the catalytic event has improved binding kinetics.

2. The method of claim 1, wherein detecting said catalytic event is by detecting one or more cleavage molecules.

3. The method of claim 1, wherein detecting said catalytic event occurs while the nucleotide phosphate is resident within the polymerase active site.

4. The method of claim 1, wherein the detection is carried out by a mechanism that provides low background and enables the detection of single molecules.

5. The method of claim 1, wherein said detection occurs while the nucleotide phosphate is resident with the polymerase, and wherein said polymerase is a member selected from the group consisting of a DNA-dependent DNA polymerase, a DNA-dependent RNA polymerase and a reverse transcriptase.

6. The method of claim 1, wherein detecting is via a mechanism selected from the group consisting of fluorescence resonance energy transfer, an electron transfer mechanism, an excited-state lifetime mechanism and a ground-state complex quenching mechanism.

7. The method of claim 1, wherein the detection is using a system or device selected from the group consisting of an optical reader, a high-efficiency photon detection system, a photodiode, a camera, a charge couple device, an intensified charge couple device, an on-chip multiplication gain charge coupled device, a near-field scanning microscope, a far-field confocal microscope, a microscope that detects wide-field epi-illumination, and a total internal reflection fluorescence microscope.

8. The method of claim 1, wherein detecting is performed using a detection device, and wherein the detection device is a four color single molecule imaging microscope.

9. The method of claim 1, wherein said nanoparticle is selected from the group consisting of a nucleic acid nanoparticle, a nucleic acid analog particle, a semiconductor nanoparticle, a nanocrystal, a silicon nanocrystal, a metallic nanoparticle, a silica-shell nanoparticle, a dye-doped silica-shell nanoparticle, a nanoparticle made of an organic polymer, a light-scattering nanoparticle, an electroactive nanoparticle, a coated nanoparticle, a protein nanoparticle, a fluorescent protein, and combinations thereof.

10. The method of claim 1, wherein said nanoparticle is selected from the group consisting of a 20 nm polystyrene sphere, a semiconductor nanocrystal, a quantum dot, a resonance light scattering (RLS) metal particle, a dye-doped silica shell nanoparticle, and a silicon crystal nanoparticle.

11. The method of claim 1, wherein said nanoparticle further comprises a dye.

12. The method of claim 11, wherein said dye is attached to the surface of said nanoparticle.

13. The method of claim 11, wherein said dye is embedded in said nanoparticle.

14. The method of claim 11, wherein said dye and said nucleotide phosphates are attached to said nanoparticle through said linker.

15. The method of claim 10, wherein said nanoparticle surface is coated with a reactive functional group.

16. The method of claim 15, wherein said reactive functional group is a haloacetyl group, an amine, a thiol, a phosphate, a carboxylate, or a combination thereof.

17. The method of claim 1, wherein said nucleotide phosphates are selected from the group consisting of a nucleotide diphosphate, a nucleotide triphopshate (NTP), a nucleotide tetraphosphate, a nucleotide pentaphosphate and a nucleotide hexaphosphate.

18. The method of claim 17, wherein said nucleotide phosphates are nucleotide triphosphates (NTPs).

19. The method of claim 10, wherein said linker comprises polyethylene glycol (PEG).

20. The method of claim 11, wherein said dye is a fluorescent dye.

21. The method of claim 9, wherein said semiconductor nanoparticle is a quantum dot.

* * * * *

SEQUENCE LISTING

```
<160> NUMBER OF SEQ ID NOS: 5

<210> SEQ ID NO 1
<211> LENGTH: 23
<212> TYPE: PRT
<213> ORGANISM: Artificial Sequence
<220> FEATURE:
<223> OTHER INFORMATION: Description of Artificial Sequence:polymerase
      biotin loop
<220> FEATURE:
<221> NAME/KEY: MOD_RES
<222> LOCATION: (13)
<223> OTHER INFORMATION: Xaa = Lys modified by biotin

<400> SEQUENCE: 1

Ser Ser Gly Gly Leu Asn Asp Ile Phe Glu Ala Gln Xaa Ile Glu Trp
  1               5                  10                  15

His Glu Asp Thr Gly Ser Ser
             20

<210> SEQ ID NO 2
<211> LENGTH: 85
<212> TYPE: DNA
<213> ORGANISM: Artificial Sequence
<220> FEATURE:
<223> OTHER INFORMATION: Description of Artificial Sequence:oligo 1,
      oligonucleotide for template construction, 5'
      phosphate-labeled oligo containing regions of
      inverted repeat DNA

<400> SEQUENCE: 2
cagcgtgcca cgctgggacg gtgcgagcct tggttaggct cgcaccgtcc cagcgtggca        60
cgctgcgacc ctgcgacggt gccac                                             85

<210> SEQ ID NO 3
<211> LENGTH: 86
<212> TYPE: DNA
<213> ORGANISM: Artificial Sequence
<220> FEATURE:
<223> OTHER INFORMATION: Description of Artificial Sequence:oligo 2,
      oligonucleotide for template construction, 5'
      phosphate-labeled oligo containing regions of
      inverted repeat DNA

<400> SEQUENCE: 3
gctcgcaggc tggcgcgccg tttcggatcg ggttagggtc ctatttcggc gcgccagcct        60
gcgagcgtgg caccgtcgca gggtcg                                            86

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:primer 1
      used for rolling circle replication
```

```
<400> SEQUENCE: 4
taggaccata acccgatccg                                                    20

<210> SEQ ID NO 5
<211> LENGTH: 173
<212> TYPE: DNA
<213> ORGANISM: Artificial Sequence
<220> FEATURE:
<223> OTHER INFORMATION: Description of Artificial Sequence:single
      hairpin unit
<220> FEATURE:
<221> NAME/KEY: modified_base
<222> LOCATION: (173)
<223> OTHER INFORMATION: n = unknown

<400> SEQUENCE: 5
tttcggcgcg ccagcctgcg agcgtggcac cgtcgcaggg tcgcagcgtg ccacgctggg        60
acggtgcgag ccttggttag gctcgcaccg tcccagcgtg gcacgctgcg accctgcgac       120
ggtgccacgc tcgcaggctg gcgcgccgtt tcggatcggg ttagggtcct aan              173
```